(12) United States Patent
Sharifi-Mehr et al.

(10) Patent No.: US 10,603,182 B2
(45) Date of Patent: Mar. 31, 2020

(54) SPINAL IMPLANT WITH FLUID DELIVERY CAPABILITIES

(71) Applicant: Stryker European Holdings I, LLC, Kalamazoo, MI (US)

(72) Inventors: Amir Ali Sharifi-Mehr, Bloomingdale, NJ (US); Oliver Buchert, Franklin Lakes, NJ (US); Richard Michael Afflitto, Pompton Plains, NJ (US); Philippe Emmanuel Pare, Allendale, NJ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 57 days.

(21) Appl. No.: 14/994,697

(22) Filed: Jan. 13, 2016

(65) Prior Publication Data

US 2016/0199190 A1 Jul. 14, 2016

Related U.S. Application Data

(60) Provisional application No. 62/103,270, filed on Jan. 14, 2015.

(51) Int. Cl.
*A61F 2/44* (2006.01)
(52) U.S. Cl.
CPC ............... *A61F 2/442* (2013.01); *A61F 2/44* (2013.01); *A61F 2002/4475* (2013.01)
(58) Field of Classification Search
CPC ............... A61F 2002/4475; A61F 2/44; A61F 2/4455–447; A61F 2/4614; A61B 17/8802–8805; A61B 17/8842
See application file for complete search history.

(56) References Cited

U.S. PATENT DOCUMENTS

| | | | |
|---|---|---|---|
| 3,852,045 | A | 12/1974 | Wheeler et al. |
| 3,855,638 | A | 12/1974 | Pilliar |
| 4,612,160 | A | 9/1986 | Donlevy et al. |
| 1,853,489 | A | 3/1987 | Tronzo |
| 4,718,914 | A | 1/1988 | Frey et al. |
| 5,071,437 | A | 12/1991 | Steffee |
| 5,156,628 | A | 10/1992 | Kranz |

(Continued)

FOREIGN PATENT DOCUMENTS

| | | |
|---|---|---|
| DE | 10052008 C1 | 8/2002 |
| DE | 202013007361 U1 | 3/2014 |

(Continued)

OTHER PUBLICATIONS

Extended European Search Report for Application No. EP16171066 dated Dec. 14, 2016.

(Continued)

*Primary Examiner* — Jacqueline T Johanas
(74) *Attorney, Agent, or Firm* — Lerner, David, Littenberg, Krumholz & Mentlik, LLP

(57) ABSTRACT

A spinal implant that allows for fluid injection of material is disclosed. The implant includes a fitting with a passage and holes that are in fluid communication with the passage. The holes extend through upper and lower surfaces and/or into a central cavity of the implant. The implant allows for material to be introduced into the implant after initial implantation thereof. Methods of implanting the implant are also disclosed.

16 Claims, 29 Drawing Sheets

(56) References Cited

U.S. PATENT DOCUMENTS

| | | | |
|---|---|---|---|
| 5,180,381 A | 1/1993 | Aust et al. | |
| 5,263,986 A | 11/1993 | Noiles et al. | |
| 5,370,692 A | 12/1994 | Fink et al. | |
| 5,443,514 A | 8/1995 | Steffee | |
| 5,458,643 A | 10/1995 | Oka et al. | |
| 5,489,308 A * | 2/1996 | Kuslich | A61F 2/30744 |
| | | | 606/247 |
| 5,504,300 A | 4/1996 | Devanathan et al. | |
| 5,672,284 A | 9/1997 | Devanathan et al. | |
| 5,702,455 A * | 12/1997 | Saggar | A61F 2/44 |
| | | | 623/17.15 |
| 5,723,011 A | 3/1998 | Devanathan et al. | |
| 5,734,959 A | 3/1998 | Krebs et al. | |
| 5,768,134 A | 6/1998 | Swaelens et al. | |
| 5,776,199 A * | 7/1998 | Michelson | A61F 2/30744 |
| | | | 606/247 |
| 5,961,554 A | 10/1999 | Janson et al. | |
| 6,039,761 A * | 3/2000 | Li | A61B 17/70 |
| | | | 623/17.16 |
| 6,152,927 A | 11/2000 | Farris et al. | |
| 6,193,721 B1 | 2/2001 | Michelson | |
| 6,293,949 B1 | 9/2001 | Justis et al. | |
| 6,447,547 B1 * | 9/2002 | Michelson | A61F 2/30744 |
| | | | 623/17.11 |
| 6,454,769 B2 | 9/2002 | Wagner et al. | |
| 6,471,725 B1 | 10/2002 | Ralph et al. | |
| 6,485,521 B1 | 11/2002 | Say et al. | |
| 6,503,250 B2 | 1/2003 | Paul | |
| 6,533,786 B1 | 3/2003 | Needham et al. | |
| 6,533,818 B1 | 3/2003 | Weber et al. | |
| 6,547,823 B2 * | 4/2003 | Scarborough | A61F 2/30771 |
| | | | 623/17.16 |
| 6,572,654 B1 | 6/2003 | Santilli | |
| 6,623,525 B2 | 9/2003 | Ralph et al. | |
| 6,673,075 B2 | 1/2004 | Santilli | |
| 6,740,186 B2 | 5/2004 | Hawkins et al. | |
| 6,767,367 B1 | 7/2004 | Michelson | |
| 6,790,233 B2 | 9/2004 | Brodke et al. | |
| 6,863,689 B2 | 3/2005 | Ralph et al. | |
| 6,890,335 B2 | 5/2005 | Grabowski et al. | |
| 6,890,355 B2 * | 5/2005 | Michelson | A61F 2/28 |
| | | | 606/247 |
| 6,945,448 B2 | 9/2005 | Medlin et al. | |
| 6,970,233 B2 | 11/2005 | Blatchford | |
| 7,044,972 B2 | 5/2006 | Mathys, Jr. et al. | |
| 7,118,580 B1 | 10/2006 | Beyersdorff et al. | |
| 7,135,042 B2 | 11/2006 | Stoll | |
| 7,169,150 B2 | 1/2007 | Shipp et al. | |
| 7,238,203 B2 | 7/2007 | Bagga et al. | |
| 7,241,313 B2 | 7/2007 | Unwin et al. | |
| 7,255,713 B2 | 8/2007 | Malek | |
| 7,278,997 B1 | 10/2007 | Mueller et al. | |
| 7,303,564 B2 | 12/2007 | Freid et al. | |
| 7,497,876 B2 | 3/2009 | Tuke et al. | |
| 7,500,976 B2 | 3/2009 | Suh | |
| 7,501,073 B2 | 3/2009 | Wen et al. | |
| 7,563,284 B2 | 7/2009 | Coppes et al. | |
| 7,625,375 B2 | 12/2009 | Garden et al. | |
| 7,635,447 B2 | 12/2009 | Hamman et al. | |
| 7,662,186 B2 | 2/2010 | Bagga et al. | |
| 7,670,359 B2 | 3/2010 | Yundt | |
| 7,670,375 B2 | 3/2010 | Schaller | |
| 7,766,947 B2 | 8/2010 | Hawkes et al. | |
| 7,857,839 B2 | 12/2010 | Duong et al. | |
| 7,862,597 B2 | 1/2011 | Gause et al. | |
| 7,883,661 B2 | 2/2011 | Hamman et al. | |
| 7,918,382 B2 | 4/2011 | Charlebois et al. | |
| 7,922,765 B2 | 4/2011 | Reiley | |
| 8,043,346 B2 | 10/2011 | Markworth | |
| 8,083,796 B1 | 12/2011 | Raiszadeh et al. | |
| 8,092,499 B1 | 1/2012 | Roth | |
| 8,105,366 B2 | 1/2012 | Null et al. | |
| 8,123,808 B2 * | 2/2012 | Dewey | A61F 2/44 |
| | | | 623/17.12 |
| 8,167,946 B2 * | 5/2012 | Michelson | A61F 2/4611 |
| | | | 623/17.11 |
| 8,191,760 B2 | 6/2012 | Charlebois et al. | |
| 8,202,305 B2 | 6/2012 | Reiley | |
| 8,231,676 B2 | 7/2012 | Trudeau et al. | |
| 8,236,034 B2 | 8/2012 | Binder et al. | |
| 8,262,737 B2 | 9/2012 | Bagga et al. | |
| 8,266,780 B2 | 9/2012 | Bollinger et al. | |
| 8,268,100 B2 | 9/2012 | O'Neill et al. | |
| 8,303,879 B2 | 11/2012 | Bertele et al. | |
| 8,308,805 B2 * | 11/2012 | Lynn | A61F 2/442 |
| | | | 623/17.16 |
| 8,343,224 B2 | 1/2013 | Lynn et al. | |
| 8,361,126 B2 | 1/2013 | Perrow et al. | |
| 8,361,150 B2 | 1/2013 | Zhang et al. | |
| 8,361,153 B2 | 1/2013 | Ralph et al. | |
| 8,361,380 B2 | 1/2013 | Hamman et al. | |
| 8,388,667 B2 | 3/2013 | Reiley et al. | |
| 8,403,969 B2 | 3/2013 | Wallenstein et al. | |
| 8,403,991 B2 | 3/2013 | Ullrich, Jr. et al. | |
| 8,414,648 B2 | 4/2013 | Reiley | |
| 8,414,650 B2 | 4/2013 | Bertele et al. | |
| 8,414,651 B2 | 4/2013 | Tyber et al. | |
| 8,414,654 B1 | 4/2013 | Ganey | |
| 8,414,820 B2 | 4/2013 | Bertele et al. | |
| 8,419,777 B2 | 4/2013 | Walker et al. | |
| 8,425,570 B2 | 4/2013 | Reiley | |
| 8,425,604 B2 | 4/2013 | Trieu | |
| 8,435,301 B2 | 5/2013 | Gerber et al. | |
| 8,435,302 B2 | 5/2013 | Ulrich, Jr. et al. | |
| 8,444,693 B2 | 5/2013 | Reiley | |
| 8,470,004 B2 | 6/2013 | Reiley | |
| 8,470,042 B2 | 6/2013 | Zhang et al. | |
| 8,480,749 B2 | 7/2013 | Ullrich, Jr. et al. | |
| 8,486,115 B2 | 7/2013 | Fisher et al. | |
| 8,496,710 B2 | 7/2013 | Bagga et al. | |
| 8,500,782 B2 | 8/2013 | Kovach et al. | |
| 8,500,811 B2 | 8/2013 | Blain et al. | |
| 8,500,819 B2 | 8/2013 | Meridew et al. | |
| 8,530,560 B2 | 9/2013 | Kerr et al. | |
| 8,535,354 B2 | 9/2013 | Cummins | |
| 8,545,568 B2 | 10/2013 | Ulrich, Jr. et al. | |
| 8,551,173 B2 | 10/2013 | Lechmann et al. | |
| 8,551,176 B2 | 10/2013 | Ullrich, Jr. et al. | |
| 8,556,981 B2 | 10/2013 | Jones et al. | |
| 8,562,684 B2 | 10/2013 | Ullrich, Jr. et al. | |
| 8,562,685 B2 | 10/2013 | Ullrich, Jr. et al. | |
| 8,585,765 B2 | 11/2013 | Ullrich, Jr. et al. | |
| 8,585,766 B2 | 11/2013 | Ullrich, Jr. et al. | |
| 8,585,767 B2 | 11/2013 | Ullrich, Jr. et al. | |
| 8,591,590 B2 | 11/2013 | Ullrich, Jr. et al. | |
| 8,617,246 B2 | 12/2013 | Malone | |
| 8,617,248 B2 | 12/2013 | Ullrich, Jr. et al. | |
| 8,632,604 B2 | 1/2014 | Brooks | |
| 8,636,803 B2 * | 1/2014 | Hibri | A61F 2/441 |
| | | | 623/17.12 |
| 8,663,332 B1 * | 3/2014 | To | A61F 2/442 |
| | | | 623/17.16 |
| 8,673,016 B2 | 3/2014 | Liu | |
| 8,709,088 B2 * | 4/2014 | Kleiner | A61F 2/447 |
| | | | 606/94 |
| 8,734,462 B2 | 5/2014 | Reiley et al. | |
| 8,747,412 B2 | 6/2014 | Bae et al. | |
| 8,758,442 B2 | 6/2014 | Ullrich, Jr. et al. | |
| 8,758,443 B2 | 6/2014 | Ullrich, Jr. et al. | |
| 8,814,939 B2 | 8/2014 | Ullrich, Jr. et al. | |
| 8,814,978 B2 | 8/2014 | Hamman et al. | |
| 8,821,555 B2 | 9/2014 | Bae et al. | |
| 8,827,986 B2 | 9/2014 | Shachar et al. | |
| 8,834,571 B2 | 9/2014 | Bagga et al. | |
| 8,840,623 B2 | 9/2014 | Reiley | |
| 8,845,736 B2 | 9/2014 | Zhang et al. | |
| 8,864,831 B2 | 10/2014 | Lee et al. | |
| 8,870,957 B2 * | 10/2014 | Vraney | A61F 2/447 |
| | | | 606/246 |
| 8,900,277 B2 | 12/2014 | Perrow et al. | |
| 8,906,093 B2 | 12/2014 | Malone | |
| 8,906,095 B2 | 12/2014 | Christensen et al. | |
| 8,940,053 B2 | 1/2015 | Ullrich, Jr. et al. | |

(56) References Cited

U.S. PATENT DOCUMENTS

| | | |
|---|---|---|
| 8,979,934 B2 | 3/2015 | Kirschman |
| 8,985,430 B2 | 3/2015 | Charlebois et al. |
| 8,992,619 B2 | 3/2015 | Patterson et al. |
| 9,060,876 B1* | 6/2015 | To .......................... A61F 2/442 |
| 9,078,718 B2 | 7/2015 | Campbell |
| 9,089,428 B2 | 7/2015 | Bertele et al. |
| 9,173,692 B1* | 11/2015 | Kaloostian ......... A61B 17/8685 |
| 9,320,549 B2 | 4/2016 | Fraser et al. |
| 9,375,237 B2 | 6/2016 | Keegan et al. |
| 9,381,044 B2 | 7/2016 | Robinson et al. |
| 9,387,087 B2 | 7/2016 | Tyber |
| 9,615,733 B2 | 4/2017 | Nottmeier |
| 9,629,664 B2 | 4/2017 | Altarac et al. |
| 9,655,665 B2 | 5/2017 | Perrow |
| 9,730,807 B2 | 8/2017 | Donaldson |
| 9,782,270 B2* | 10/2017 | Wickham ................. A61F 2/447 |
| 9,925,051 B2 | 3/2018 | Bae et al. |
| 10,070,970 B2* | 9/2018 | Lynn ....................... A61F 2/447 |
| 2002/0004683 A1 | 1/2002 | Michelson |
| 2003/0055505 A1 | 3/2003 | Sicotte et al. |
| 2003/0083748 A1* | 5/2003 | Lee ......................... A61F 2/447 |
| | | 623/17.16 |
| 2004/0059318 A1 | 3/2004 | Zhang et al. |
| 2004/0122426 A1 | 6/2004 | Michelson |
| 2004/0133279 A1 | 7/2004 | Krueger et al. |
| 2004/0181226 A1 | 9/2004 | Michelson |
| 2004/0193269 A1 | 9/2004 | Fraser et al. |
| 2004/0204712 A1 | 10/2004 | Kolb et al. |
| 2004/0210218 A1 | 10/2004 | Dixon et al. |
| 2004/0215195 A1 | 10/2004 | Shipp et al. |
| 2004/0220566 A1 | 11/2004 | Bray |
| 2004/0220571 A1 | 11/2004 | Assaker et al. |
| 2004/0225360 A1* | 11/2004 | Malone .............. A61B 17/7064 |
| | | 623/17.11 |
| 2004/0258732 A1* | 12/2004 | Shikinami ............. A61L 27/446 |
| | | 424/426 |
| 2005/0033294 A1 | 2/2005 | Garden et al. |
| 2005/0049593 A1 | 3/2005 | Duong et al. |
| 2005/0049595 A1 | 3/2005 | Suh et al. |
| 2005/0070900 A1* | 3/2005 | Serhan ............... A61B 17/3468 |
| | | 623/17.12 |
| 2005/0075633 A1 | 4/2005 | Ross |
| 2005/0123672 A1 | 6/2005 | Justin et al. |
| 2005/0143820 A1 | 6/2005 | Zucherman et al. |
| 2005/0154460 A1* | 7/2005 | Yundt ...................... A61F 2/441 |
| | | 623/17.11 |
| 2005/0177238 A1 | 8/2005 | Khandkar et al. |
| 2005/0216081 A1 | 9/2005 | Taylor |
| 2006/0036250 A1 | 2/2006 | Lange et al. |
| 2006/0089656 A1 | 4/2006 | Allard et al. |
| 2006/0116770 A1* | 6/2006 | White ......................... A61F 2/44 |
| | | 623/17.16 |
| 2006/0122603 A1 | 6/2006 | Kolb |
| 2006/0195097 A1 | 8/2006 | Evans et al. |
| 2006/0293668 A1 | 12/2006 | May et al. |
| 2007/0073404 A1 | 3/2007 | Rashbaum et al. |
| 2007/0123884 A1 | 5/2007 | Abdou |
| 2007/0123985 A1 | 5/2007 | Errico et al. |
| 2007/0173816 A1 | 7/2007 | Metz-Stavenhagen |
| 2007/0173940 A1 | 7/2007 | Hestad et al. |
| 2007/0179609 A1 | 8/2007 | Goble et al. |
| 2008/0097435 A1 | 4/2008 | DeRidder et al. |
| 2008/0161927 A1 | 7/2008 | Savage et al. |
| 2008/0183292 A1 | 7/2008 | Trieu |
| 2008/0262623 A1 | 10/2008 | Bagga et al. |
| 2008/0269756 A1 | 10/2008 | Tomko et al. |
| 2008/0306595 A1 | 12/2008 | McLeod et al. |
| 2009/0093885 A1 | 4/2009 | Levieux et al. |
| 2009/0105832 A1 | 4/2009 | Allain et al. |
| 2009/0112323 A1 | 4/2009 | Hestad et al. |
| 2009/0138015 A1 | 5/2009 | Conner et al. |
| 2009/0198184 A1* | 8/2009 | Martin ..................... A61B 17/60 |
| | | 604/151 |
| 2009/0240333 A1 | 9/2009 | Trudeau et al. |
| 2009/0287257 A1 | 11/2009 | Hagen |
| 2009/0306717 A1 | 12/2009 | Kercher et al. |
| 2010/0042218 A1 | 2/2010 | Nebosky et al. |
| 2010/0042221 A1 | 2/2010 | Boyd |
| 2010/0076559 A1 | 3/2010 | Bagga et al. |
| 2010/0094426 A1 | 4/2010 | Grohowski, Jr. et al. |
| 2010/0137916 A1 | 6/2010 | Hynes et al. |
| 2010/0137990 A1 | 6/2010 | Apatsidis et al. |
| 2010/0256773 A1 | 10/2010 | Thijs et al. |
| 2010/0262244 A1 | 10/2010 | Savage-Erickson et al. |
| 2010/0262245 A1* | 10/2010 | Alfaro .................... A61F 2/4465 |
| | | 623/17.16 |
| 2010/0268343 A1 | 10/2010 | Dewey et al. |
| 2011/0004256 A1* | 1/2011 | Biedermann ........ A61B 17/7098 |
| | | 606/301 |
| 2011/0071635 A1 | 3/2011 | Zhang et al. |
| 2011/0106159 A1 | 5/2011 | Nazeck |
| 2011/0160866 A1 | 6/2011 | Laurence et al. |
| 2011/0196494 A1 | 8/2011 | Yedlicka et al. |
| 2011/0282392 A1 | 11/2011 | Murphy et al. |
| 2011/0282454 A1 | 11/2011 | Ullrich, Jr. et al. |
| 2011/0301709 A1* | 12/2011 | Kraus .................... A61F 2/4465 |
| | | 623/17.11 |
| 2012/0029432 A1 | 2/2012 | Sweeney |
| 2012/0071933 A1 | 3/2012 | DeRidder |
| 2012/0078315 A1* | 3/2012 | Sweeney ............. A61B 17/8811 |
| | | 606/86 A |
| 2012/0078373 A1 | 3/2012 | Gamache et al. |
| 2012/0123544 A1* | 5/2012 | Suh ......................... A61F 2/447 |
| | | 623/17.16 |
| 2012/0215315 A1 | 8/2012 | Hochschuler et al. |
| 2012/0265306 A1 | 10/2012 | Trieu |
| 2012/0277876 A1 | 11/2012 | Ullrich, Jr. et al. |
| 2012/0303127 A1 | 11/2012 | Ullrich, Jr. et al. |
| 2012/0312778 A1 | 12/2012 | Ullrich, Jr. et al. |
| 2012/0312779 A1 | 12/2012 | Patterson et al. |
| 2012/0330420 A1 | 12/2012 | Brodke et al. |
| 2013/0123925 A1 | 5/2013 | Patterson et al. |
| 2013/0184822 A1* | 7/2013 | Kleiner .................. A61F 2/4455 |
| | | 623/17.12 |
| 2013/0274886 A1 | 10/2013 | Matsumoto et al. |
| 2013/0282122 A1 | 10/2013 | Ullrich, Jr. et al. |
| 2013/0292357 A1 | 11/2013 | Ullrich, Jr. et al. |
| 2013/0304218 A1 | 11/2013 | Ullrich, Jr. et al. |
| 2013/0306591 A1 | 11/2013 | Ullrich, Jr. et al. |
| 2013/0338777 A1 | 12/2013 | Bagga et al. |
| 2014/0025169 A1 | 1/2014 | Lechmann et al. |
| 2014/0031942 A1 | 1/2014 | Ullrich, Jr. et al. |
| 2014/0046449 A1 | 2/2014 | Ullrich, Jr. et al. |
| 2014/0052258 A1* | 2/2014 | Ball ........................ A61F 2/442 |
| | | 623/17.16 |
| 2014/0114415 A1 | 4/2014 | Tyber |
| 2014/0114421 A1 | 4/2014 | Ullrich, Jr. et al. |
| 2014/0128924 A1 | 5/2014 | Perrow et al. |
| 2014/0200670 A1 | 7/2014 | Chin et al. |
| 2014/0277461 A1 | 9/2014 | Nebosky et al. |
| 2014/0277464 A1* | 9/2014 | Richter ............... A61B 17/7097 |
| | | 623/17.12 |
| 2014/0277482 A1 | 9/2014 | Gfeller et al. |
| 2014/0277491 A1 | 9/2014 | Fang et al. |
| 2014/0277511 A1 | 9/2014 | Ullrich, Jr. et al. |
| 2014/0277512 A1 | 9/2014 | Ullrich, Jr. et al. |
| 2014/0350682 A1 | 11/2014 | Bagga et al. |
| 2015/0012100 A1 | 1/2015 | Ullrich, Jr. et al. |
| 2015/0032220 A1 | 1/2015 | Tyber et al. |
| 2015/0045903 A1 | 2/2015 | Neal |
| 2015/0073422 A1 | 3/2015 | Chegini et al. |
| 2015/0157465 A1 | 6/2015 | Kirschman |
| 2015/0202047 A1 | 7/2015 | Patterson et al. |
| 2015/0202051 A1 | 7/2015 | Tanaka et al. |
| 2015/0230832 A1 | 8/2015 | Fraser et al. |
| 2016/0038301 A1 | 2/2016 | Wickham |
| 2016/0081818 A1 | 3/2016 | Waugh et al. |
| 2016/0199190 A1* | 7/2016 | Sharifi-Mehr ......... A61F 2/442 |
| | | 623/17.12 |
| 2017/0049491 A1 | 2/2017 | Ross et al. |
| 2017/0119537 A1 | 5/2017 | Tepper et al. |
| 2017/0182222 A1* | 6/2017 | Paddock .................... A61F 2/44 |

(56) References Cited

U.S. PATENT DOCUMENTS

| | | |
|---|---|---|
| 2017/0224388 A1 | 8/2017 | Walker et al. |
| 2017/0238974 A1 | 8/2017 | Konieczynski et al. |
| 2019/0008655 A1* | 1/2019 | Body .................... A61F 2/4465 |

FOREIGN PATENT DOCUMENTS

| | | |
|---|---|---|
| EP | 0505634 A1 | 9/1992 |
| WO | 2006121795 A2 | 11/2006 |
| WO | 2009099559 A2 | 8/2009 |
| WO | 2010021612 A1 | 2/2010 |
| WO | 2010028045 A1 | 3/2010 |
| WO | 2010121149 A2 | 10/2010 |
| WO | 2013133729 A1 | 9/2013 |
| WO | 2014018325 A1 | 1/2014 |

OTHER PUBLICATIONS

Karageorgiou, V., and D. Kaplan. "Porosity of 3D Biomaterial Scaffolds and Osteogenesis." Biomaterials 26.27 (2005): 5474-491.

Harris, W. H. and M. Jasty (1985). "Bone ingrowth into porous coated canine acetabular replacements: the effect of pore sizee, apposition, and dislocation." Hip: 214-34.

Kujala, S. et al (2003): "Effect of porosity on the osteointegration and bone ingrowth of a weightbearing nickel-titanium bone graft substitute", Biomaterials, 24(25), Nov. 2003, pp. 4691-4697.

Callaghan, J. J. (1993). "The clinical results and basic science of total hip arthroplasty with porous-coated prostheses." J Bone Joint Surg Am 75(2): 299-310.

Wu, s et al (2013). Porous Ti6Al4V Cage Has Better Osseointegration and Less Micromotion Than a PEEK cage in Sheep Vertebral Fusion. Artificial organs 37(12).

Bobyn, J. D., G. J. Stackpool, S. A. Hacking, M. Tanzer, and J. J. Krygier. "Characteristics of Bone Ingrowth and Interface Mechanics of a New Porous Tantalum Biomaterial." The Journal of Bone and Joint Surgery81.5 (1999): 307-14.

Bobyn JD. Next generation porous metals forbiologic fixation. In: Glassman AH, Lachiewicz PF, Tanzer, M, eds. Orthopaedic Knowledge Update: Hip and Knee Reconstruction 4. Rosemont, IL: American Academy of Orthopaedic Surgeons; 2011:45-58.

Extended European Search Report for Application No. 15161713.1 dated Jun. 29, 2015.

U.S. Appl. No. 14/994,697, filed Jan. 13, 2016.

U.S. Appl. No. 14/994,749, filed Jan. 13, 2016.

Extended European Search Report for Application No. 16151374.2 dated Jun. 8, 2016.

Extended European Search Report for Application No. 16151375 dated Jun. 8, 2016.

European Search Report for Application No. 16170075 dated Oct. 21, 2016.

Extended European Search Report for Application No. EP16189379 dated Jun. 6, 2017.

Extended European Search Report for Application No. EP16202603 dated May 31, 2017.

Australian Examination Report for AU2017216532 dated Oct. 23, 2018.

* cited by examiner

SPINAL IMPLANT WITH FLUID DELIVERY CAPABILITIES

CROSS-REFERENCE TO RELATED APPLICATION

The present application claims the benefit of the filing date of U.S. Provisional Patent Application No. 62/103,270, filed Jan. 14, 2015, the disclosure of which is hereby incorporated herein by reference.

BACKGROUND OF THE INVENTION

The present invention relates to spinal surgery, namely, the fusion of adjacent intervertebral bodies or the replacement of a vertebral body.

Back pain can be caused by many different maladies, not the least of which are problems that directly impact the intervertebral discs of the spine. Typical disc issues include, inter alia, degeneration, bulging, herniation, thinning and abnormal movement. One method of treatment of such disc problems that has been widely utilized in the field of spinal surgery is a spinal fusion procedure, whereby an affected disc is removed, and the adjacent vertebral bodies are fused together through the use of interbody spacers, implants or the like. In some instances, it may also be necessary to remove and replace an entire vertebral body. This is often accomplished through the use of a larger implant that acts to fuse together the vertebral bodies adjacent the removed vertebral body.

The aforementioned implants often rely upon mechanical features to ensure engagement between the devices and the bone of the existing vertebral bodies. This coupled with the normal compressive load of the spine acts to keep the implant in place until bone can grow from the existing vertebral bodies into and through the implant. To encourage the bone growth, the implants are often pre-loaded with bone growth promoting material and thereafter placed into the spine. Bone growth promoting material may include naturally occurring bone, artificial materials or the like.

This pre-loading of bone growth promoting material normally takes place prior to implantation of existing implants, typically on a back table of the operating room. This requires the surgeon or other medical professional to estimate the overall amount of material to be pre-loaded into the implant, which is often not an easy task. Moreover, the pre-loaded material can fall out of the implant during the implantation process. All of this has the tendency to create an inefficient surgical procedure.

Therefore, there exists a need for an improved spinal implant that overcomes the aforementioned drawbacks.

BRIEF SUMMARY OF THE INVENTION

The present application discloses several embodiment spinal implants that allow for in situ application of a material such as cement, a bone growth promoting substance, BMA, biologics, antimicrobials, antibiotics, or the like. The implants in accordance with the present invention provide a more efficient manner of providing such substances to the intervertebral space. Although implants in accordance with the present invention may widely vary from what is specifically disclosed herein, the implants generally include a passage fluidly connected to holes either on one or all of the upper and lower surfaces and interior surface of a cavity formed through the implant. The holes may be sized and/or shaped to allow for uniform flow of material introduced into the implant. While largely disclosed as an implant suitable for fusing adjacent vertebral bodies, implants in accordance with the present invention may be suited for replacement of a vertebral body. Likewise, although largely shown as being suitable for introduction into the body of a patient from a certain aspect, implants according to the present invention may be configured for introduction from any aspect.

A first aspect of the present invention is a spinal implant having an upper surface including a first hole, a lower surface including a second hole a cavity formed through the upper and lower surfaces, the cavity including a third hole and a fitting including a passage in fluid communication with the first, second and third holes.

Other embodiments of the first aspect may vary from the foregoing. For instance, the spinal implant may further include a plurality of first, second and third holes, a manifold in fluid communication with the passage, a first channel in fluid communication with the manifold and the first holes and a second channel in fluid communication with the manifold and the second holes. The first and second channels may be curved, as may the manifold be curved. The first holes, second holes, first channel and second channel may increase in size as they extend further away from the passage. The third holes may be in fluid communication with the manifold and at least one of the first and second channels. The implants may further have a porous structure at the upper and/or lower surfaces. In certain embodiments, the fitting may be a male luer fitting. An insertion tool may be engaged with the fitting. The spinal implants of the first aspect may be designed to be implanted from various aspects of a patient, including from an anterior aspect of a patient. The passage, the manifold, the first channel, the second channel and the first and second holes may be included in a fluid transfer structure. That structure may be formed separately from a remainder of the implant. The implant may further include sidewalls with windows formed therethrough, the windows in fluid communication with the cavity. A fourth hole and a fifth hole may be located within the windows and in fluid communication with the passage A second aspect of the present invention is another spinal implant having an upper surface including a plurality of first holes, a lower surface including a plurality of second holes, a cavity formed through the upper and lower surfaces and a fitting including a passage in fluid communication with the first and second holes.

Other embodiments according to the second aspect may include a manifold in fluid communication with the passage, a first channel in fluid communication with the manifold and the first holes and a second channel in fluid communication with the manifold and the second holes. A plurality of third holes may be in fluid communication with the cavity.

A third aspect of the present invention is yet another spinal implant having an upper surface, a lower surface, a cavity formed through the upper and lower surfaces, the cavity including a plurality of holes and a fitting including a passage in fluid communication with the holes.

In another embodiment according to the third aspect, the upper surface may include a plurality of second holes and the lower surface may include a plurality of third holes.

BRIEF DESCRIPTION OF THE DRAWINGS

A more complete appreciation of the subject matter of the present invention and of the various advantages thereof can be realized by reference to the following detailed description in which reference is made to the accompanying drawings in which.

DETAILED DESCRIPTION

Figure 1A:
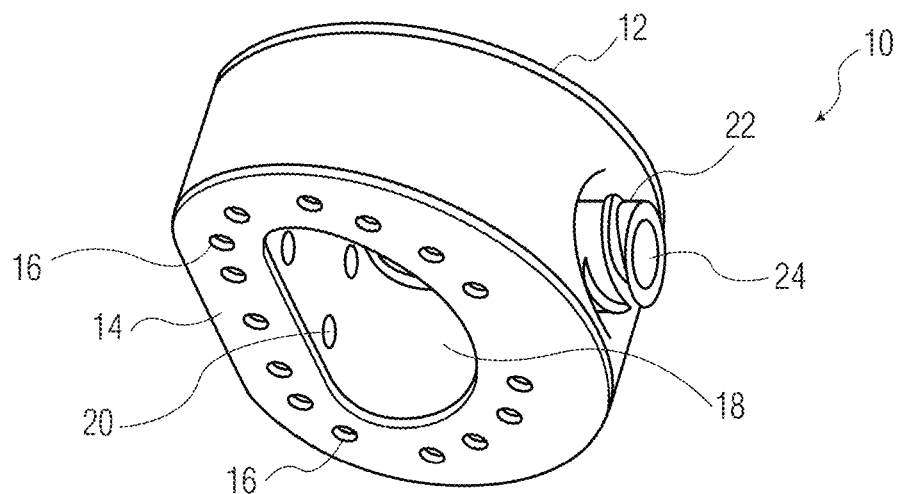
FIG. 1A is a perspective view of an implant according to one embodiment of the present invention.
Figure 1B:
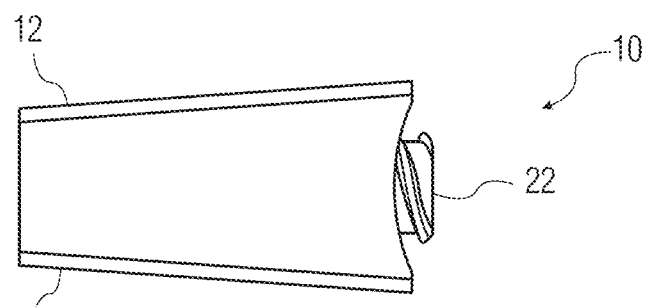
FIG. 1B is a side view of the implant of FIG. 1A.
Figure 1C:
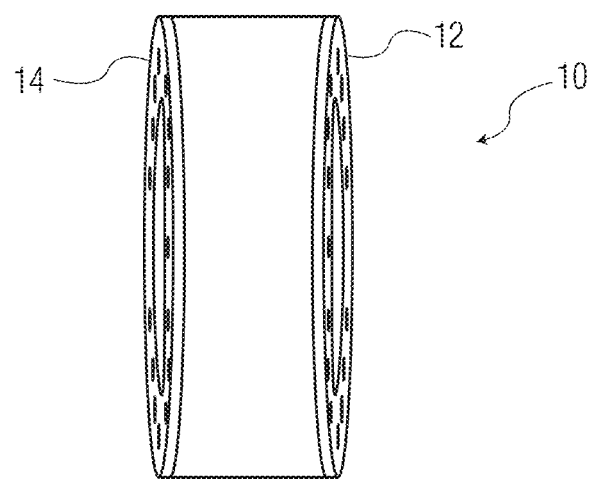
FIG. 1C is a rear view of the implant of FIG. 1A.
Figure 1D:
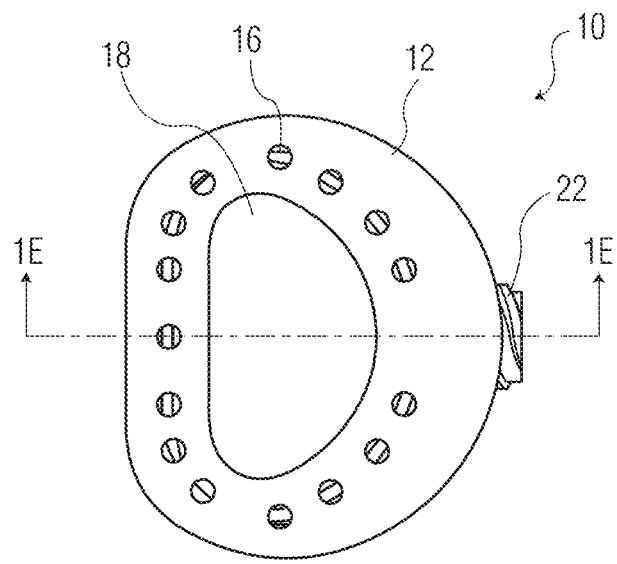
FIG. 1D is a top view of the implant of FIG. 1A.

An implant 10 according to a first embodiment of the present invention is depicted in FIGS. 1A-1G. Implant 10 is shown as an implant suitable for implantation from an anterior aspect of a patient. However, as will be readily apparent from the below discussion pertaining to other embodiments, the present invention is not limited to any particular type of implant design. Rather, it is contemplated that certain features of the present invention can be implemented in different types of implants. For instance, implants according to the present invention can be adapted for implantation from posterior, lateral, posterior-lateral aspects or the like of the patient. Moreover, implants according to the present invention may be constructed of different types of materials that are both biocompatible and suitable to withstand the natural forces of the human spine. For instance, it is contemplated that implants according to the present invention may be constructed of metallic materials such as titanium, polymeric materials such as PEEK or the like.

Implant 10 is shown including upper and lower surfaces 12 and 14, respectively. Each surface includes a plurality of holes 16 formed therethrough, although the overall number of holes and their shape may vary depending upon the particular implant and its overall size. Implant 10 also includes a central cavity 18 formed through a central portion of the implant and through each of surfaces 12 and 14. Cavity 18 can be sized and shaped differently from what is shown and can be located in other locations of implant 10. The interior of cavity 18 also includes a plurality of holes 20, which like holes 16 may vary in overall number and shape. It is also contemplated to include more than one cavity through the upper and lower surfaces of the implant.

Figure 1E:
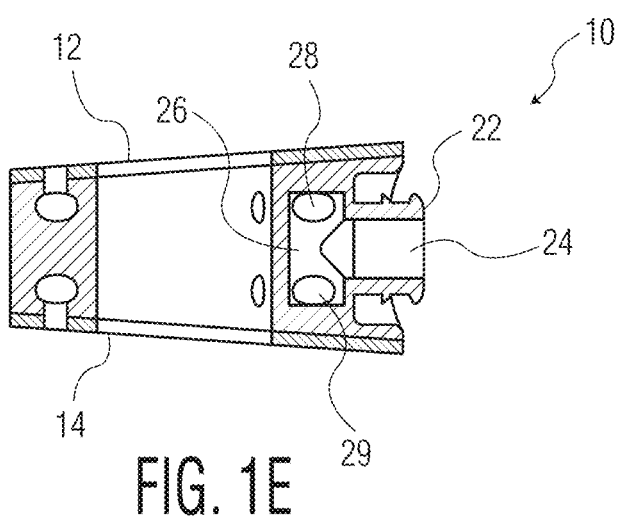
FIG. 1E is a cross-sectional view of the implant of FIG. 1A taken along line 1E-1E of FIG. 1D.
Figure 1F:
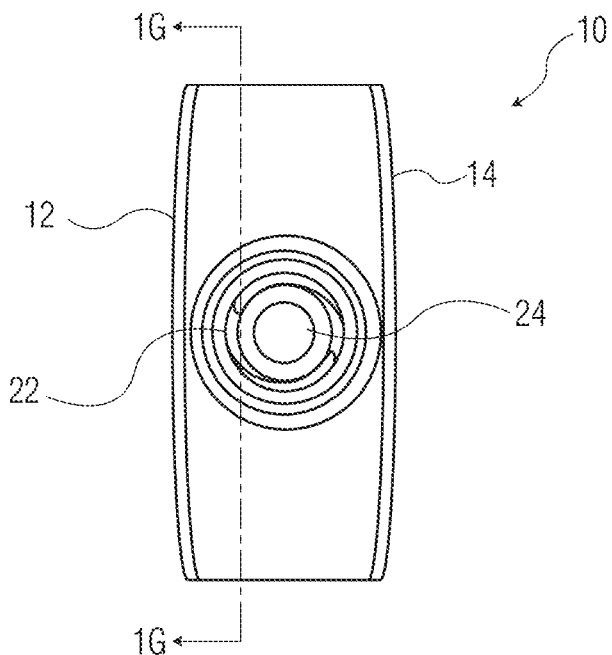
FIG. 1F is a front view of the implant of FIG. 1A.
Figure 1G:
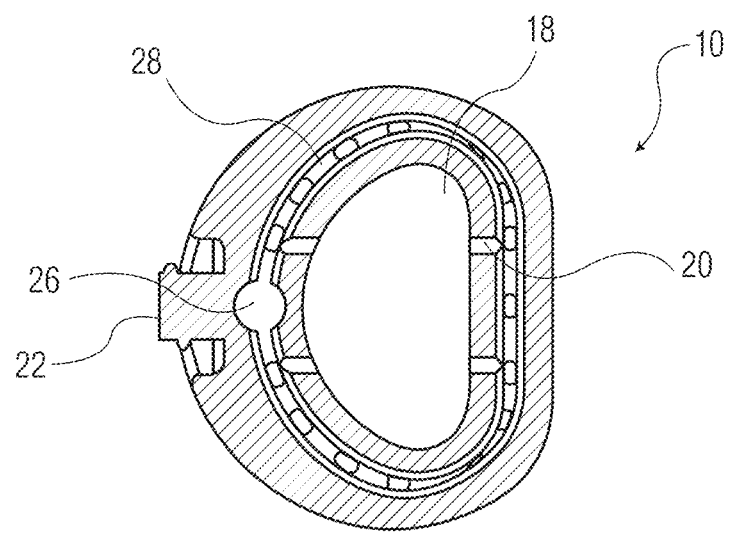
FIG. 1G is a cross-sectional view of the implant of FIG. 1A take along line 1G-1G of FIG. 1F.
Figure 2A:
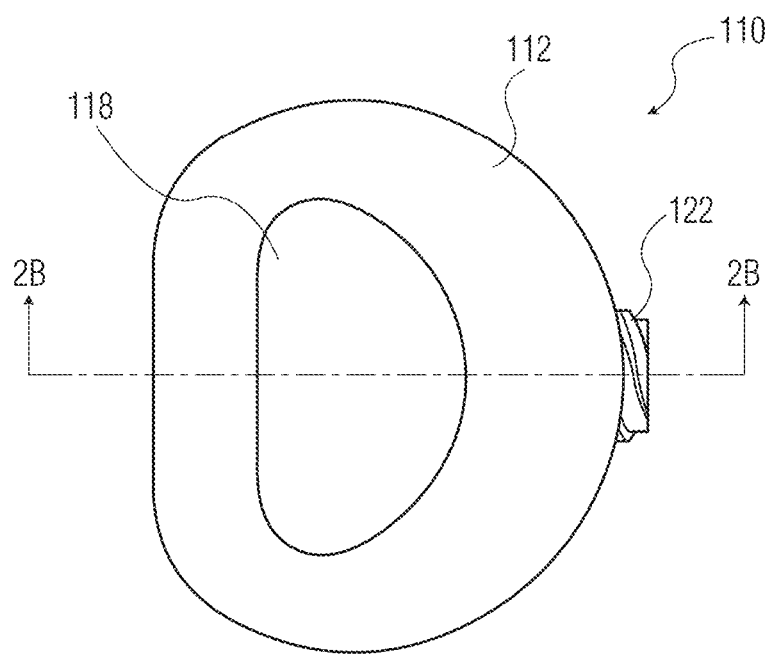
FIG. 2A is a top view of an implant according to another embodiment of the present invention.
Figure 2B:
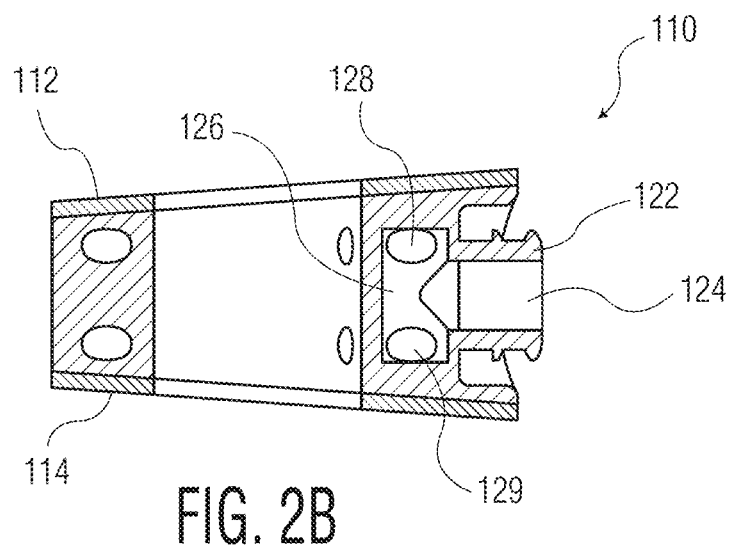
FIG. 2B is a cross-sectional view of the implant of FIG. 2A take along line 2B-2B.
Figure 2C:
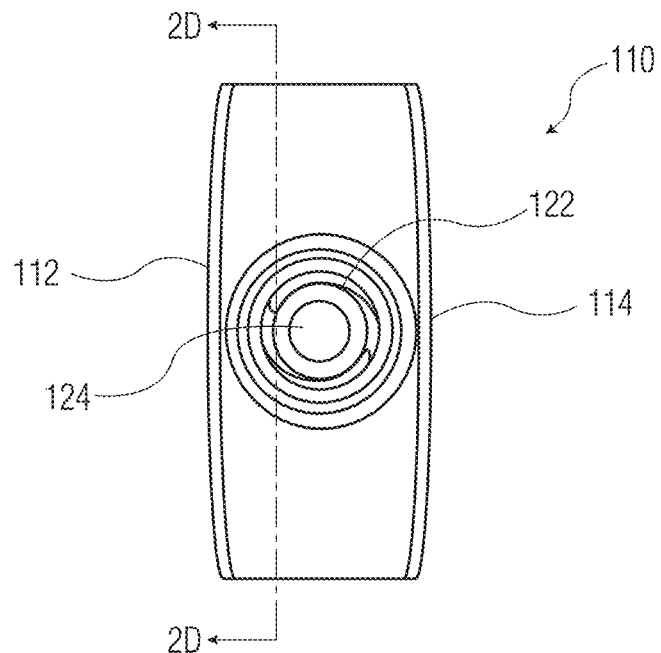
FIG. 2C is a front view of the implant of FIG. 2A.
Figure 2D:
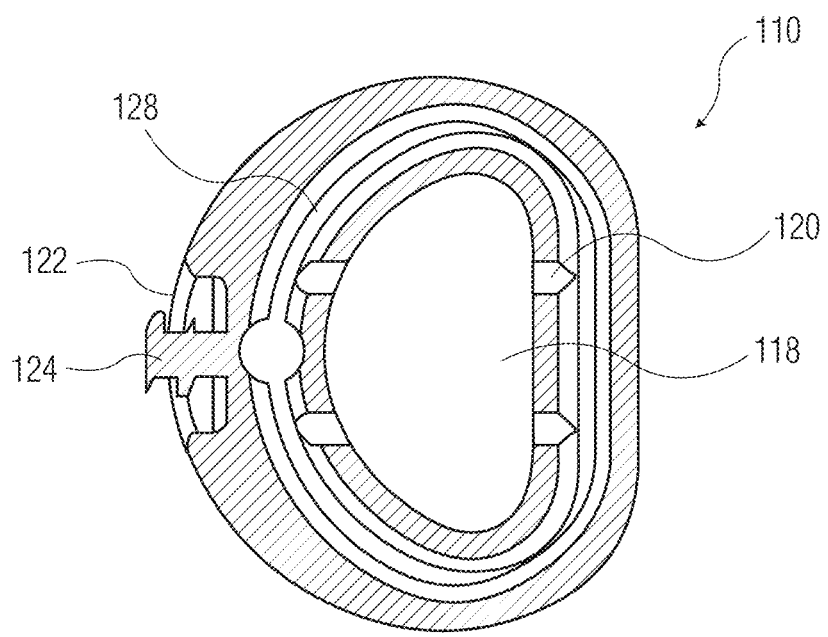
FIG. 2D is a cross-sectional view of the implant of FIG. 2A take along line 2D-2D of FIG. 2C.
Figure 3A:
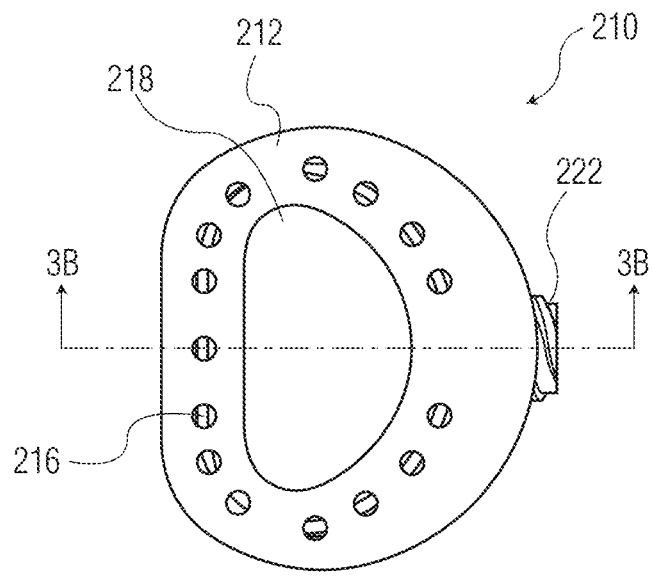
FIG. 3A is a top view of an implant according to another embodiment of the present invention.
Figure 3B:
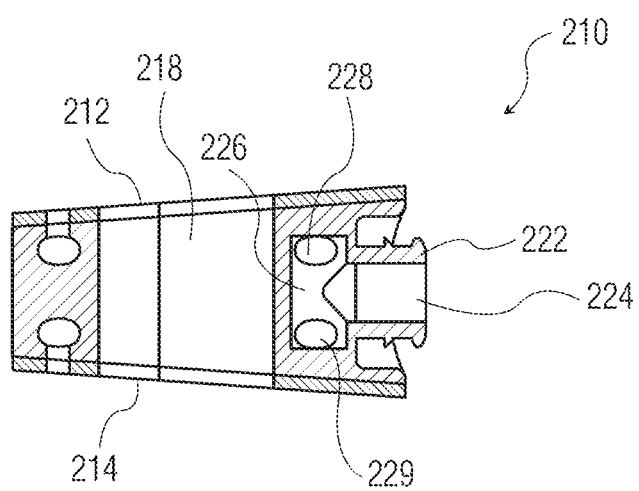
FIG. 3B is a cross-sectional view of the implant of FIG. 3A take along line 3B-3B.
Figure 3C:
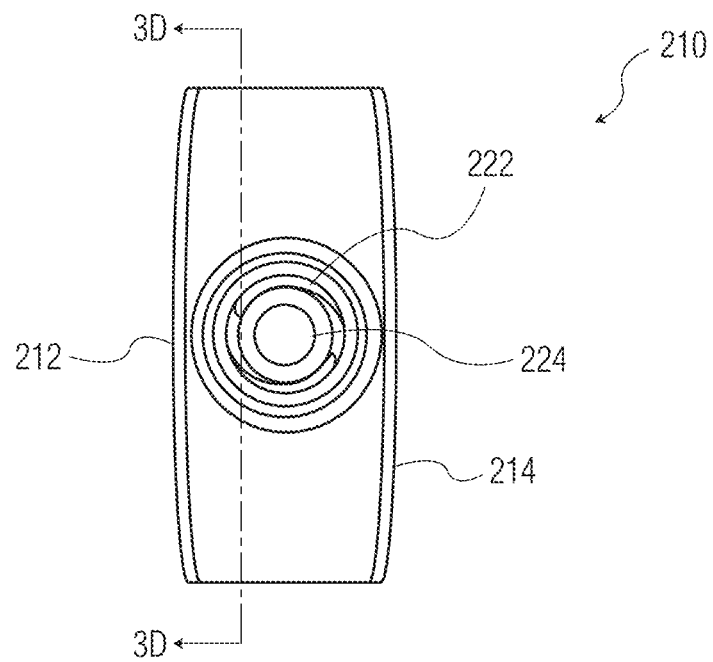
FIG. 3C is a front view of the implant of FIG. 3A.
Figure 3D:
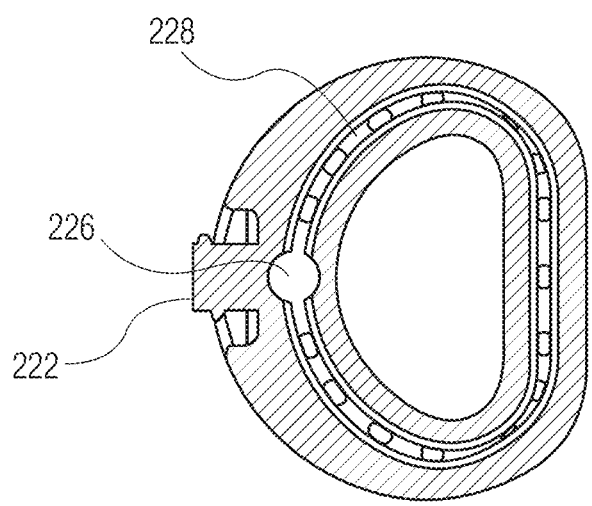
FIG. 3D is a cross-sectional view of the implant of FIG. 3A take along line 3D-3D of FIG. 3C.
Figure 4A:
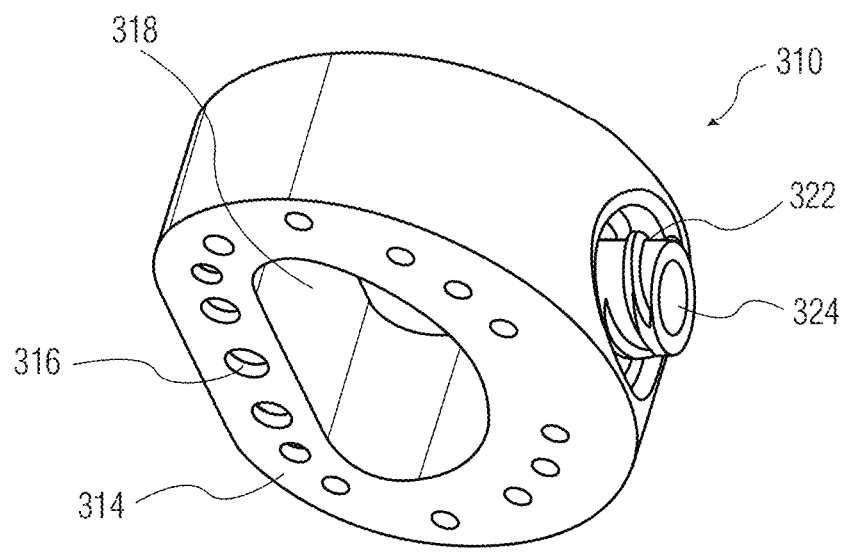
FIG. 4A is a perspective view of an implant according to another embodiment of the present invention.
Figure 4B:
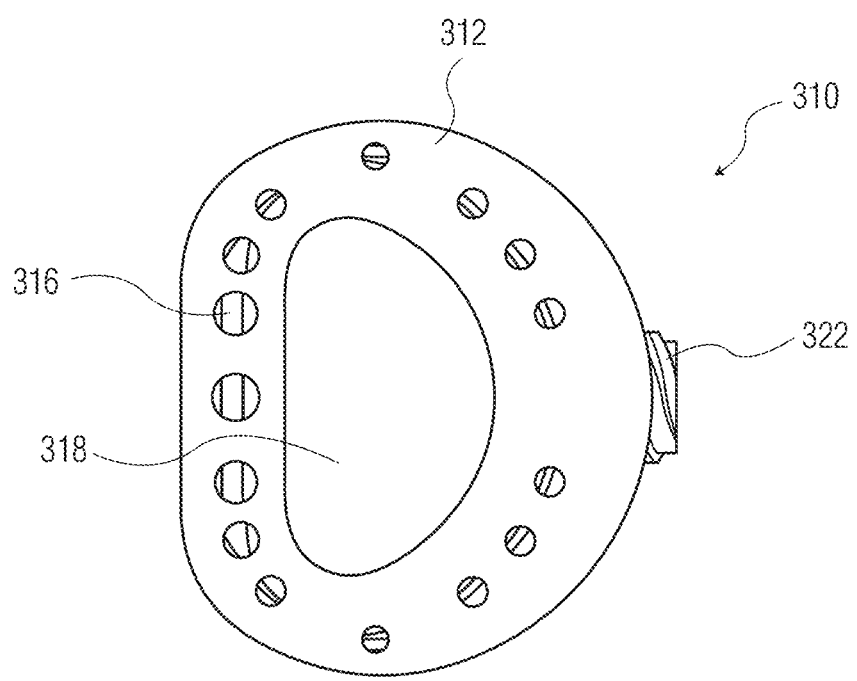
FIG. 4B is a top view of the implant of FIG. 4A.
Figure 4C:
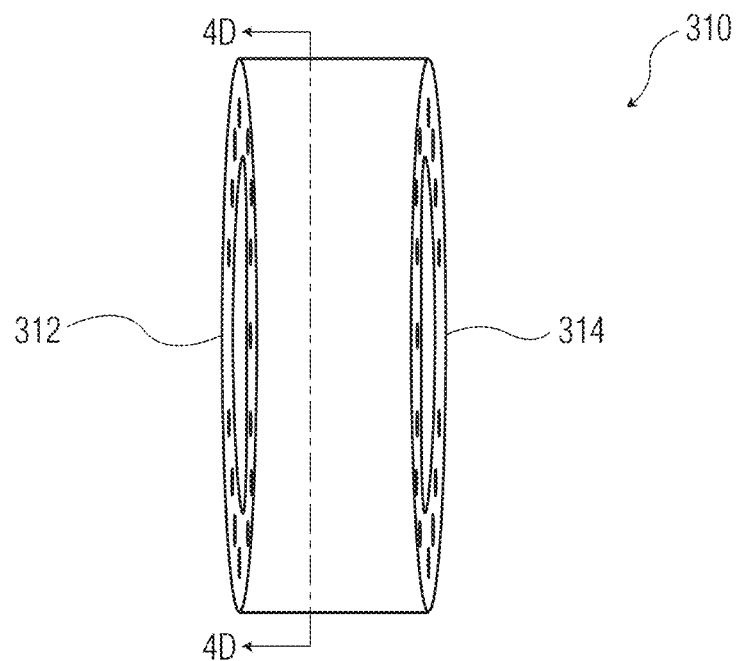
FIG. 4C is a rear view of the implant of FIG. 4A.
Figure 4D:
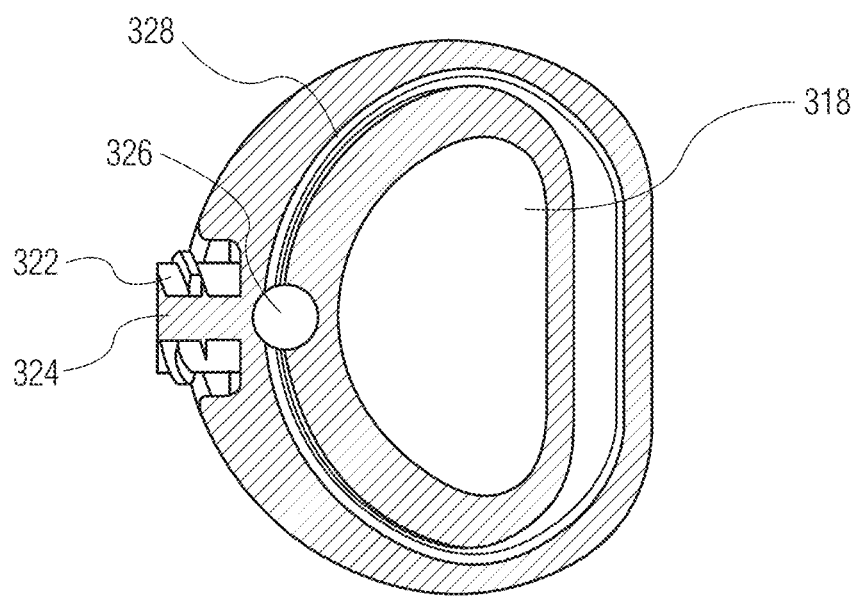
FIG. 4D is a cross-sectional view of the implant of FIG. 4A taken along line 4D-4D of FIG. 4C.
Figure 5A:
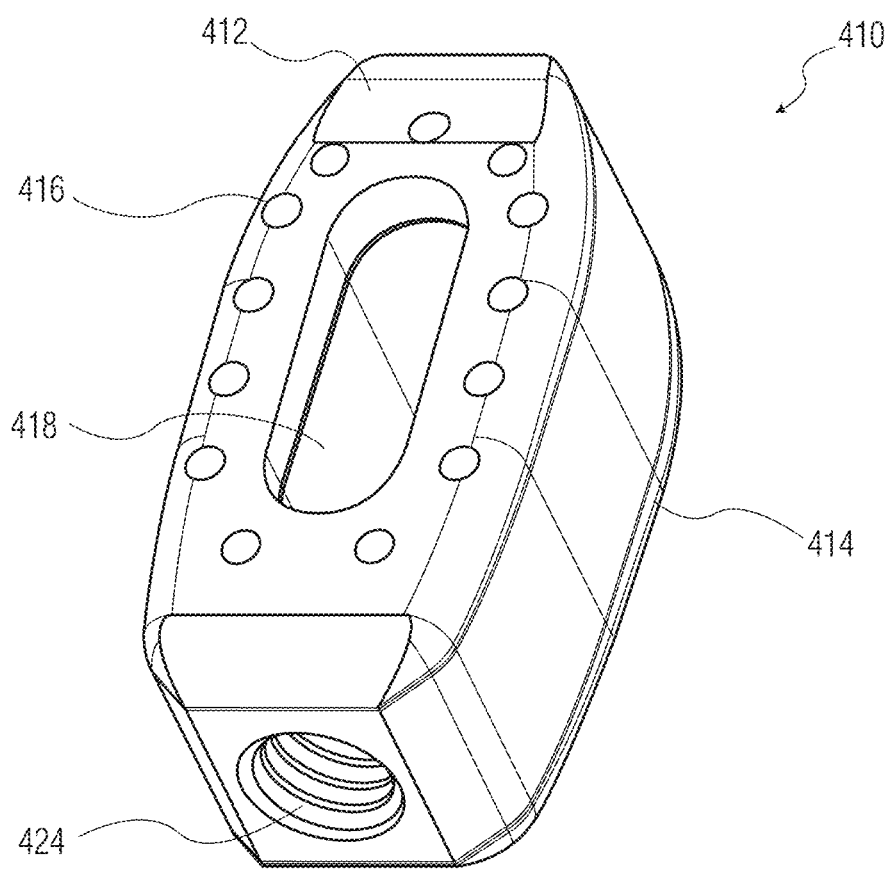
FIG. 5A is a perspective view of an implant according to another embodiment of the present invention.
Figure 5B:
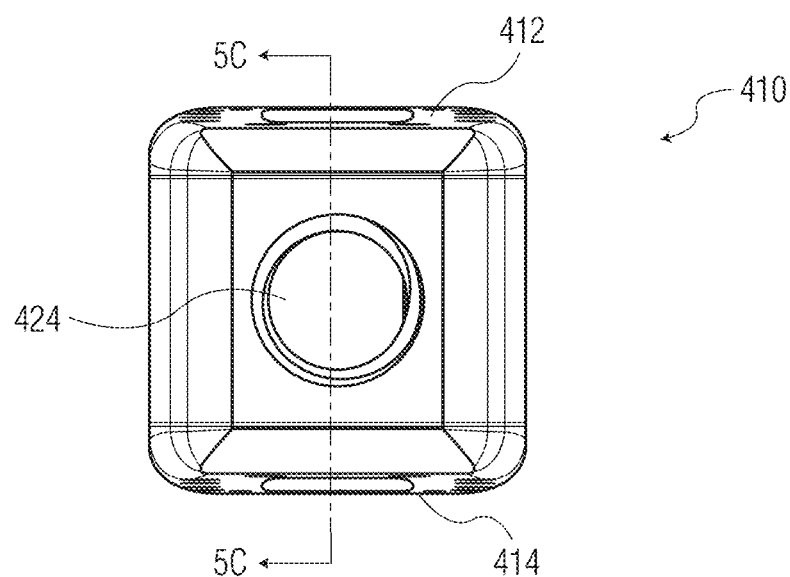
FIG. 5B is a front view of the implant of FIG. 5A.
Figure 5C:
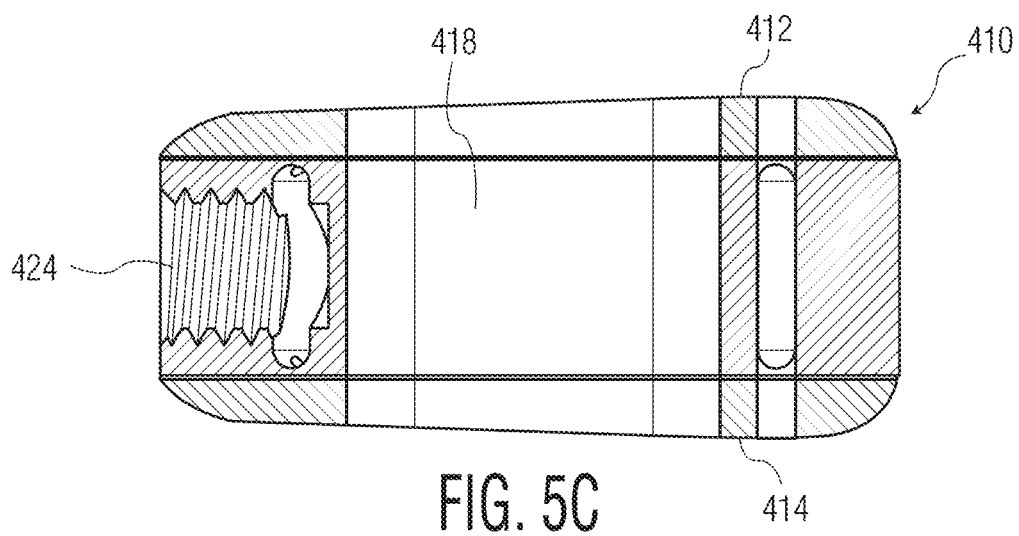
FIG. 5C is a cross-sectional view of the implant of FIG. 5A taken along line 5C-5C of FIG. 5B.
Figure 5D:
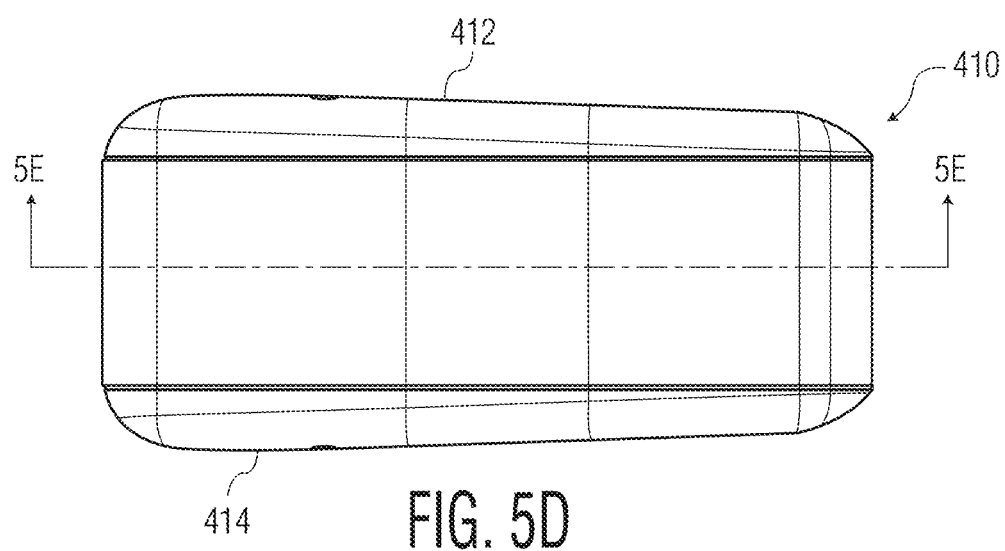
FIG. 5D is a side view of the implant of FIG. 5A.
Figure 5E:
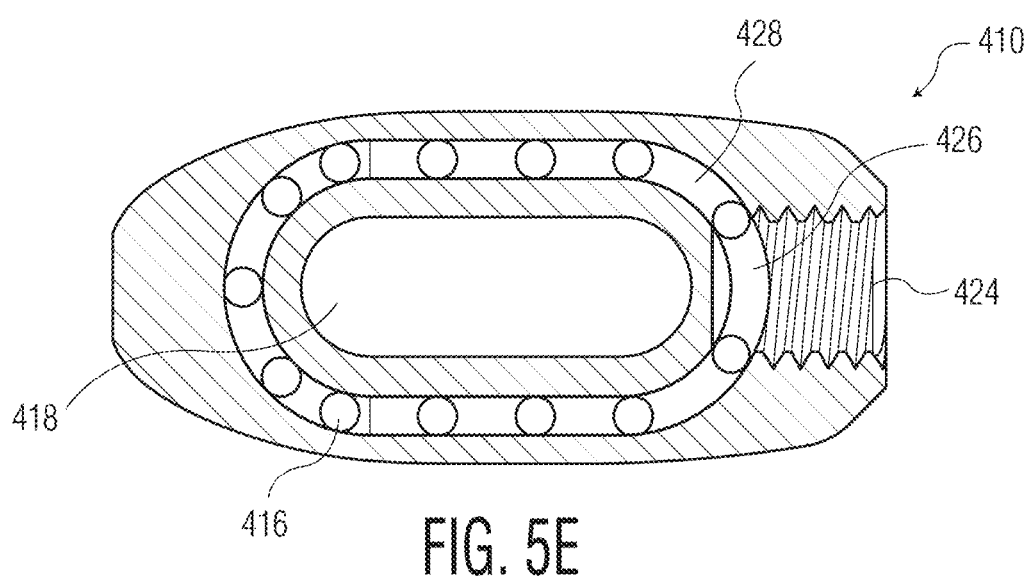
FIG. 5E is a cross-sectional view of the implant of FIG. 5A take along line 5E-5E of FIG. 5D.

Implant 10 also includes a luer fitting 22 formed in a front portion thereof. In other embodiments, a different type of fitting may be utilized (e.g., threaded, snap-fit, etc. . . . ). Fitting 22 is designed to be engaged by a similarly designed insertion tool (discussed below) and includes a passage 24. As shown in FIG. 1E, passage 24 leads to a manifold 26 fluidly connected with holes 16 and 20. In particular, as is shown in FIGS. 1E and 1G, manifold 26 is connected to holes 16 and 20 through a series of internal passages (a single flow channel 28 is shown in FIG. 1G, while two channels 28 and 29 are shown in FIG. 1E), so that material introduced through passage 24 can ultimately pass through holes 16 and 20. It is to be understood that manifold 26 actually connects with the two flow channels 28, 29, such that channel 28 is in fluid communication with holes 16 on upper surface 12 and channel 29 is in fluid communication with holes 16 on lower surface 14. The channels are also in fluid communication with holes 20 on the interior of cavity 18. This allows for bone growth promoting material, cement or the like to be introduced after implantation of implant 10, which in turn allows for both an easier implantation procedure and better application of the material to the surgical site.

FIGS. 2A-2D depict a second embodiment implant 110. Because of the similarities of implant 110 to above-discussed implant 10, like reference numerals will be utilized to describe like elements, albeit within the 100-series of numbers. For instance, implant 110 includes an upper surface 112, a lower surface 114, a cavity 118, openings 120, a fitting 122 and a passage 124. The major difference between implants 10 and 110 is that the latter does not include any holes through its upper and lower surfaces 112, 114. Thus, any material introduced through passage 124 only extends into cavity 118. This type of design results in an implanted implant more akin to traditional spinal implants, i.e., one in which grafting material or the like is only included in a central cavity or the like. Like implant 10, implant 110 includes a manifold 126 and flow channels 128, 129. Also like implant 10, implant 110 is designed to be implanted from an anterior aspect of a patient. Of course, implant 110, like all embodiment implants disclosed in the present application, could be configured for implantation from other aspects, as well as could exhibit different overall shapes and/or sizes and in its individual features.

FIGS. 3A-3D depict yet another embodiment implant 210. As with implant 110, like elements included in implant 210 will be identified with like reference numerals within the 200-series of numbers. Contrary to implant 110, implant 210 only includes holes 216 through upper and lower surfaces 212, 214. There are no holes included within cavity 218. Therefore, material introduced through passage 224 only extends to those upper and lower surfaces. Implant 210 is best suited for situations in which the implant is to be cemented in place between vertebral bodies. Cement injected through passage 224 extends to the interface between upper and lower surfaces 212, 214 and the vertebrae. Cavity 218 could separately be packed with bone growth promoting materials or the like, but such is up to the surgeon. It is also contemplated to provide an implant 210 without a cavity 218. Such an embodiment could include additional holes 216 on its upper and lower surfaces 212, 214.

FIGS. 4A-4D depict yet another embodiment implant 310, which is closest in design to implant 210. Implant 310 only includes holes 316 formed through its upper and lower surfaces 312, 314, with none being formed in cavity 318. However, holes 316, as well as flow channel 328 exhibit varying sizes. More specifically, holes 316 and flow channel 328 increase in size as they progress from passage 324. This increase in size is aimed at ensuring balanced fluid flow. In other words, the design is such that each of holes 316 get the same amount of fluid flow of material, thus ensuring even distribution of cement or other materials introduced through passage 324. Of course, the same concept may be employed in implants like above discussed implants 10, 110, where holes also extend into the central cavities of the implants.

FIGS. 5A-5E depict a PLIF-style (i.e., best suited for implantation from a posterior lateral aspect of a patient) implant 410 in accordance with the present invention. This is one example of how the overall implant design can vary from those anterior implants that are described above. Aside from the overall difference in shape, implant 410 includes an internally threaded passage 424 in lieu of a luer fitting or the like. Otherwise, implant 410 provides the similar functionality to that of above-discussed implant 210. Of course, any of the aforementioned variations could be applied to implant 410. For instance, cavity 418 could include holes in fluid communication with passage 424.

Figure 6A:
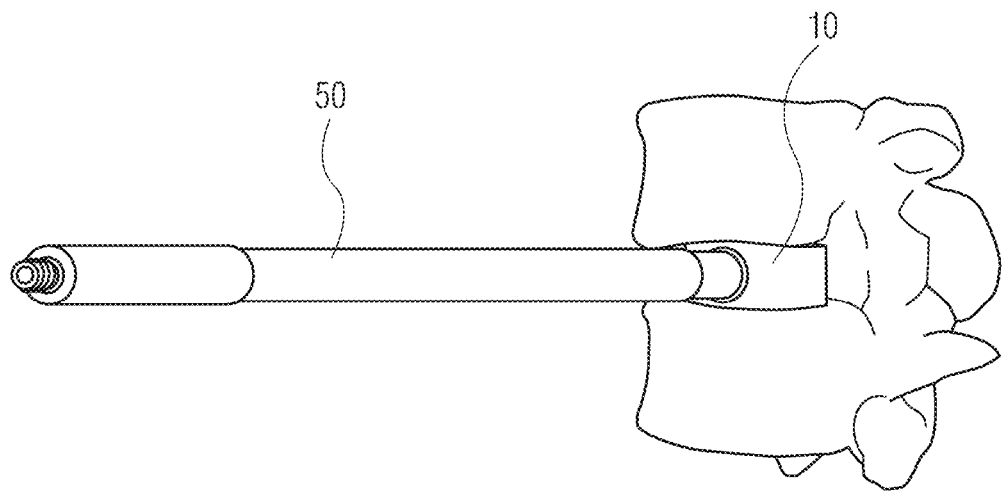
FIG. 6A depicts placement of an implant according to the present invention between adjacent vertebrae of the spine.

The use of implants according to the present invention is depicted in FIGS. 6A-6G. For ease of describing the method of use, implant 10 will be referred to. However, it is contemplated that any of the above-described implants, or variations thereof, could be utilized in such use. As shown in FIG. 6A implant 10 is first connected with an insertion tool 50. The latter is designed so as to rigidly engage implant 10, including, for instance, a female luer fitting 52 (best shown in FIGS. 6B-6D). Tool 50 also includes an internal passage 54 for allowing material to be introduced through passage 24 of implant 10 when the tool is connected thereto. Although tool 50 is depicted as including a threaded end opposite to fitting 52, many different configurations are contemplated. Essentially, tool 50 must be connected, either removably or integral with a source of material. Many different designs for such connection are contemplated, as are the sources that provide the material. For instance, it is contemplated to provide a source of material that is pressurized or capable of being pressurized to allow deployment through passage 24.

Figure 6B:
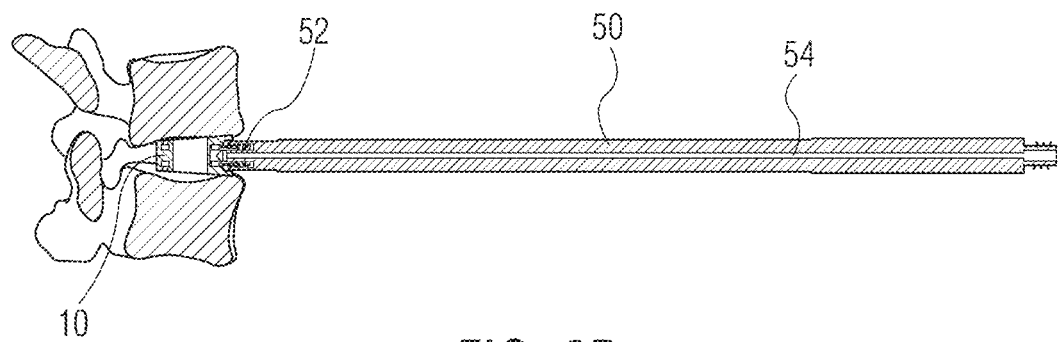
FIG. 6B is a cross-sectional view of the placement depicted in FIG. 6A.
Figure 6C:
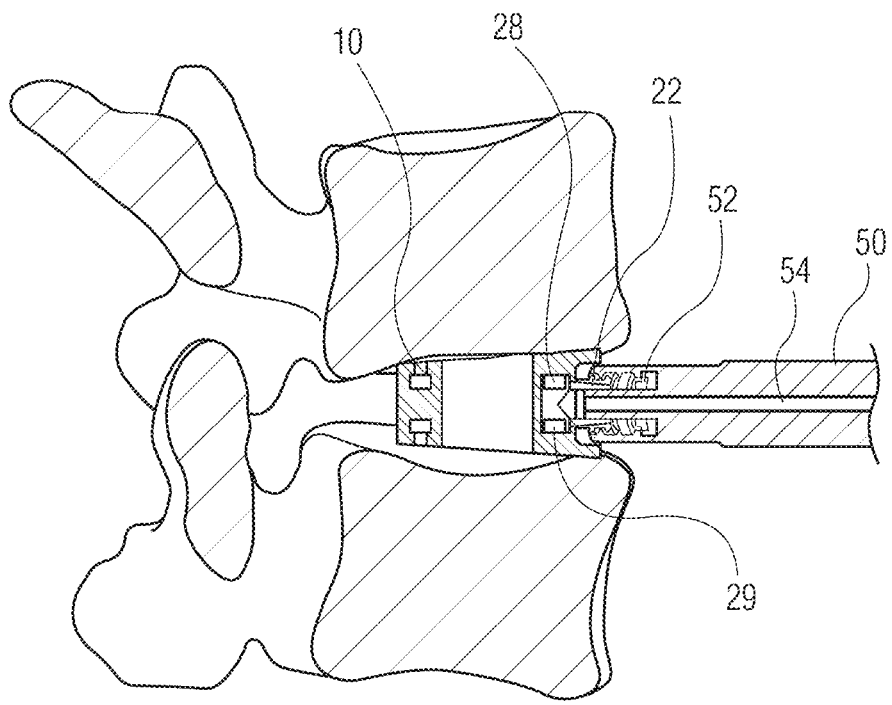
FIG. 6C is an enlarged cross-sectional view of the placement shown in FIG. 6B.
Figure 6D:
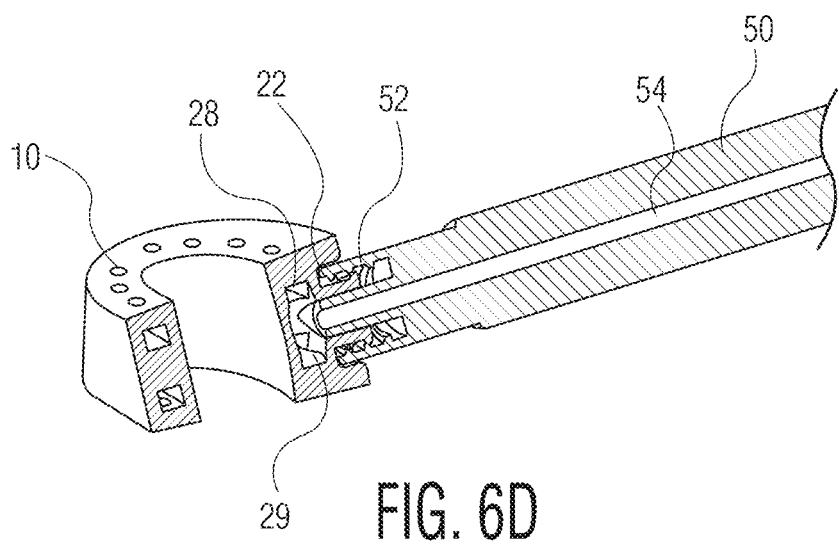
FIG. 6D is a cross-sectional view of an implant according to the present invention engaged with an insertion tool.
Figure 6E:
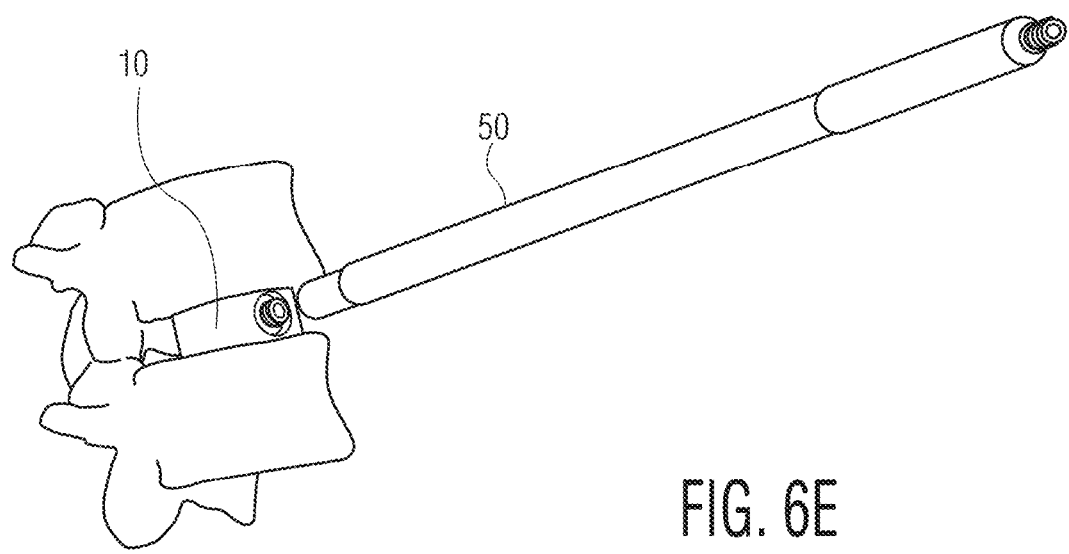
FIG. 6E depicts removal of an insertion tool subsequent to placement of an implant according to the present invention between adjacent vertebrae.
Figure 6F:
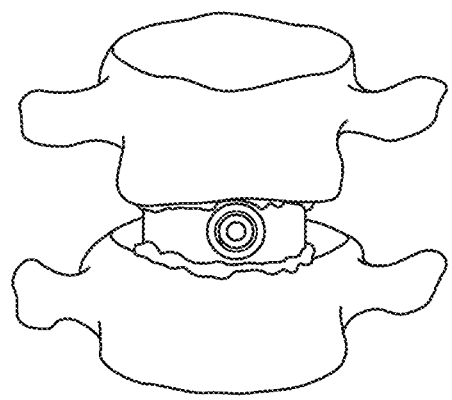
FIG. 6F illustrates an implanted implant according to the present invention subsequent to injection of a fluid or material therein.
Figure 6G:
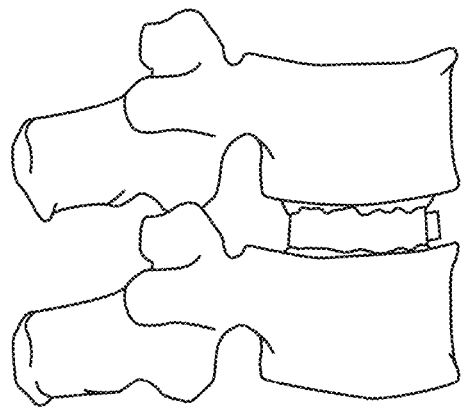
FIG. 6G is an x-ray view of the implant of FIG. 6F.

With implant 10 connected to tool 50, the latter may be manipulated to place the former between vertebral bodies, as is shown in FIGS. 6A-6C. Although the vertebral bodies shown are naturally adjacent to one another, it is contemplated that implant 10 may be sized and shaped to be placed between vertebral bodies that have become adjacent by virtue of the removal of another vertebral body. Once implant 10 is placed, material may be introduced through passage 54 of tool 50 and into implant 10. The above-discussed passage 24, channels 28, 29 and holes 16, 20 of implant 10 allow for such material to ultimately extend through upper and lower surfaces 12, 14 and/or into cavity 18. FIGS. 6F and 6G, for instance, depict an implant according to the present invention which has been implanted between two artificial bodies. Cement was thereafter introduced and is shown extending through upper and lower surfaces of the implant and into the artificial bodies. This depicts a scenario where an implant like above-discussed implant 210 is initially fixed in place through the use of cement. Finally, FIG. 6E depicts removal of tool 50 from implant 10.

Figure 7A:
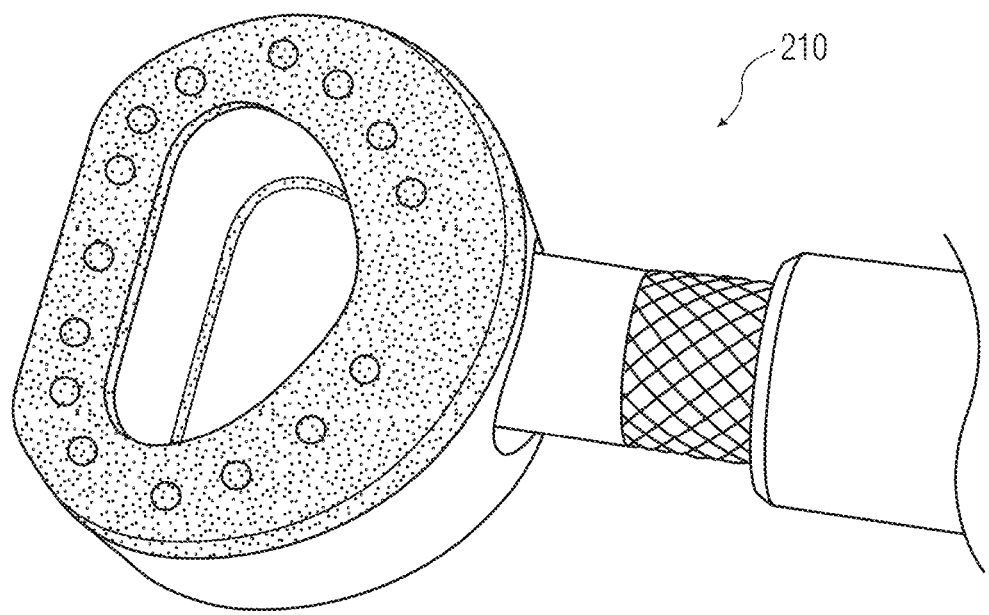
FIG. 7A illustrates a 3D printed implant according to another embodiment of the present invention with an insertion instrument attached thereto.
Figure 7B:
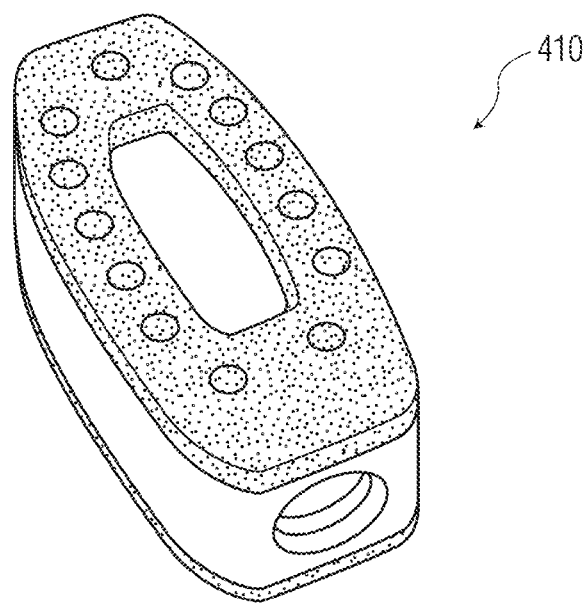
FIG. 7B illustrates a 3D printed implant according to another embodiment of the present invention.

FIGS. 7A and 7B depict 3D printed versions of implant 210 and implant 410, respectively. As shown, these versions of the implants include porous upper and lower surfaces, as can be created through the use of a 3D printing process such as is disclosed in U.S. Pat. Nos. 7,537,664 and 8,147,861; U.S. Patent Application Publications Nos. 2006/0147332, 2007/0142914, 2008/0004709; and U.S. patent application Ser. Nos. 13/441,154 and 13/618,218, the disclosures of which are hereby incorporated by reference herein. The solid portions of the implants can also be formed through the use of similar procedures. It is to be understood that creating implants according to the present invention via a 3D printing may require that the design be modified to allow for such a process. For instance, it is difficult, if not impossible, to create a surface directly over a void when using a 3D printing process. Therefore, the various manifolds, channels and passages may be curved or radiused to permit creation via the 3D printing process. It is also contemplated to form any porous region via any other suitable process, for example, a laser etching procedure.

Figure 8A:
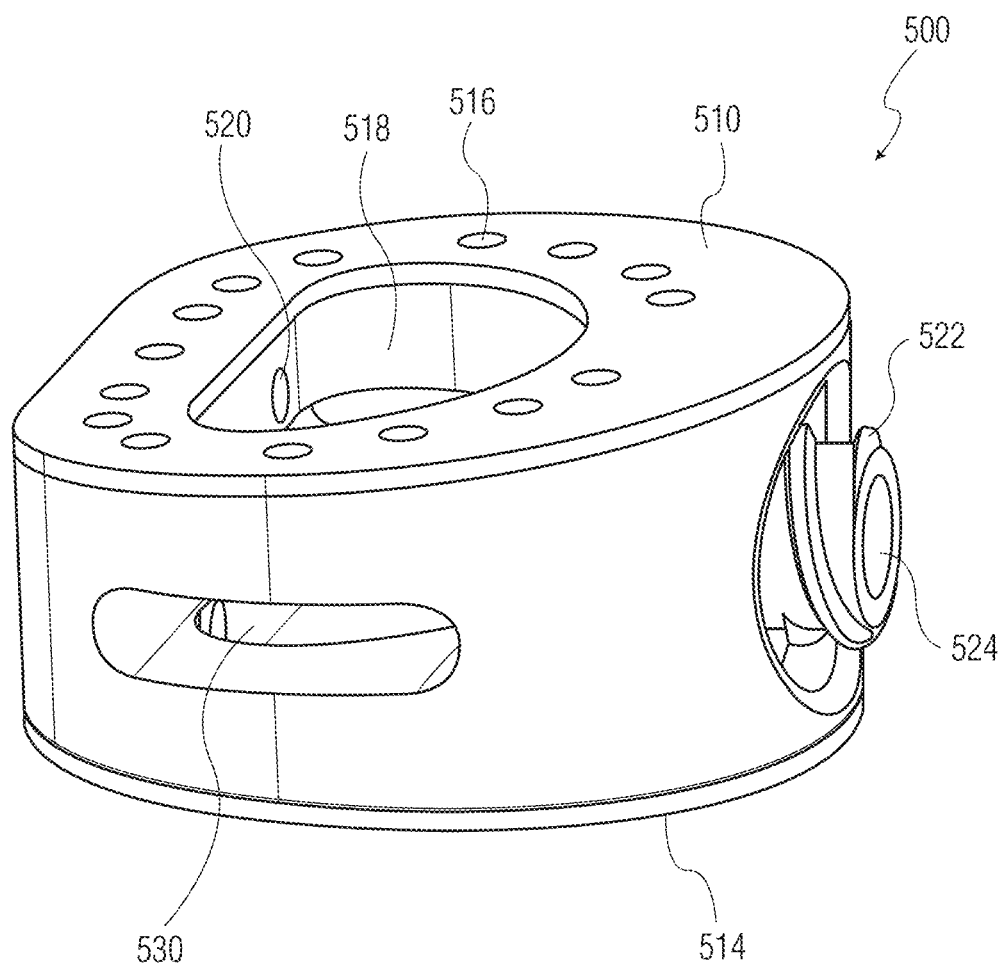
FIG. 8A is a perspective view of another implant embodiment of the present invention.
Figure 8B:
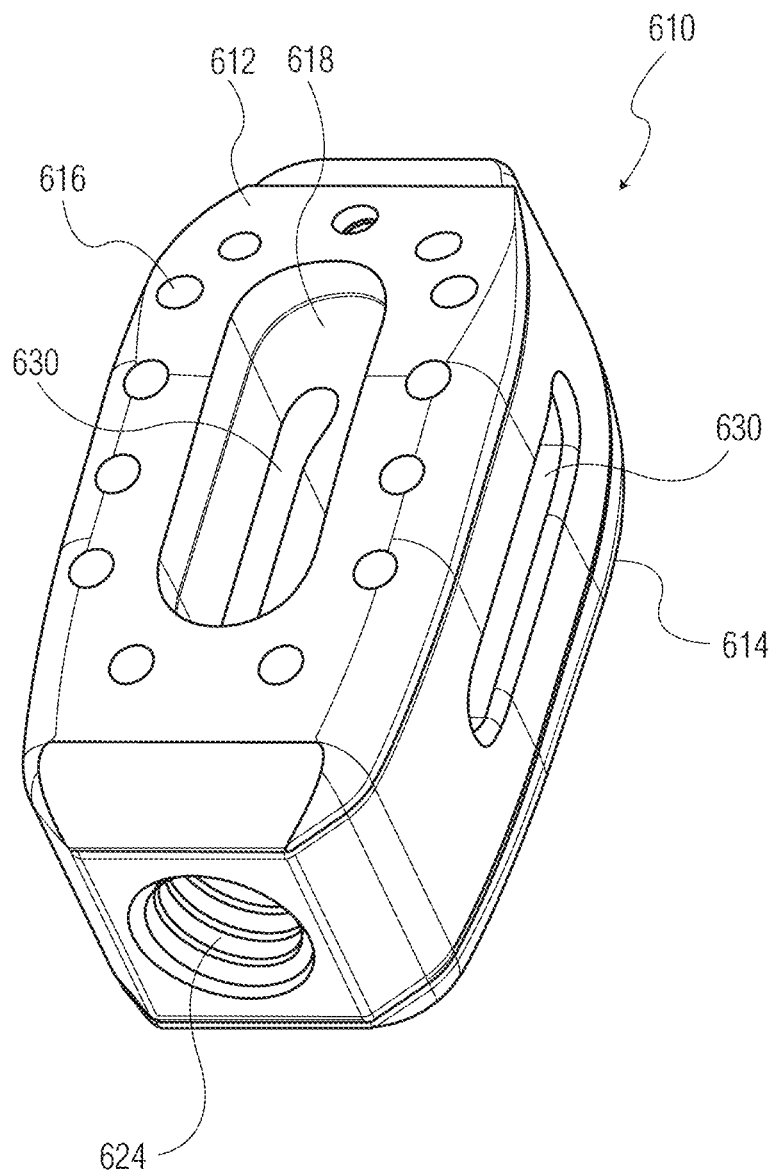
FIGS. 8B-8C depict yet another implant embodiment of the present invention.
Figure 8C:
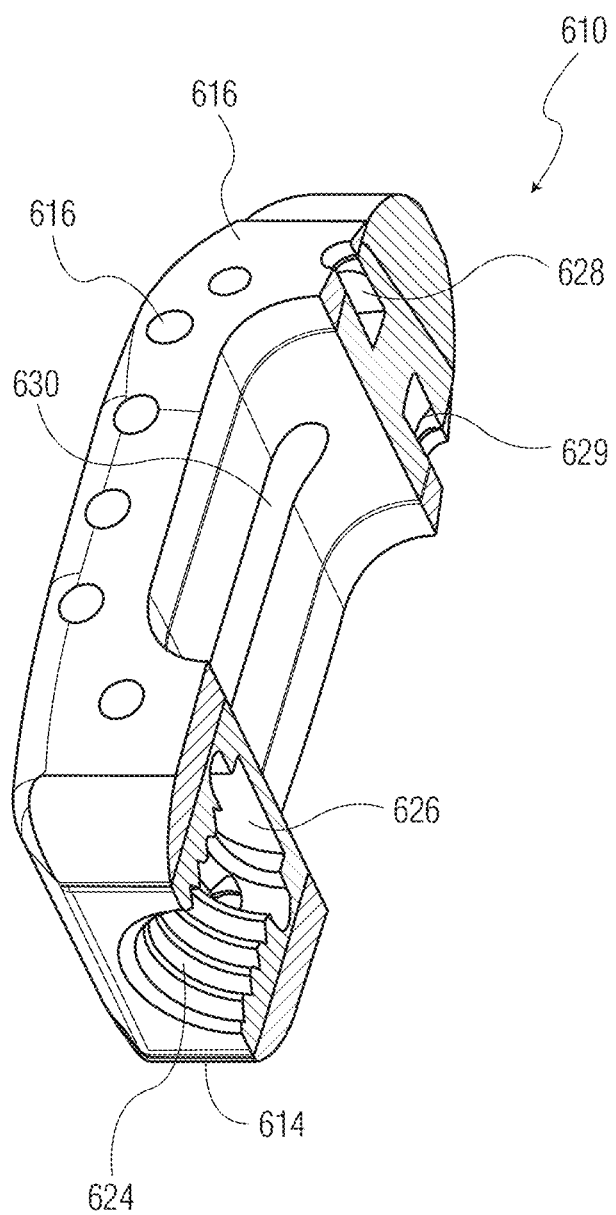
Figure 8D:
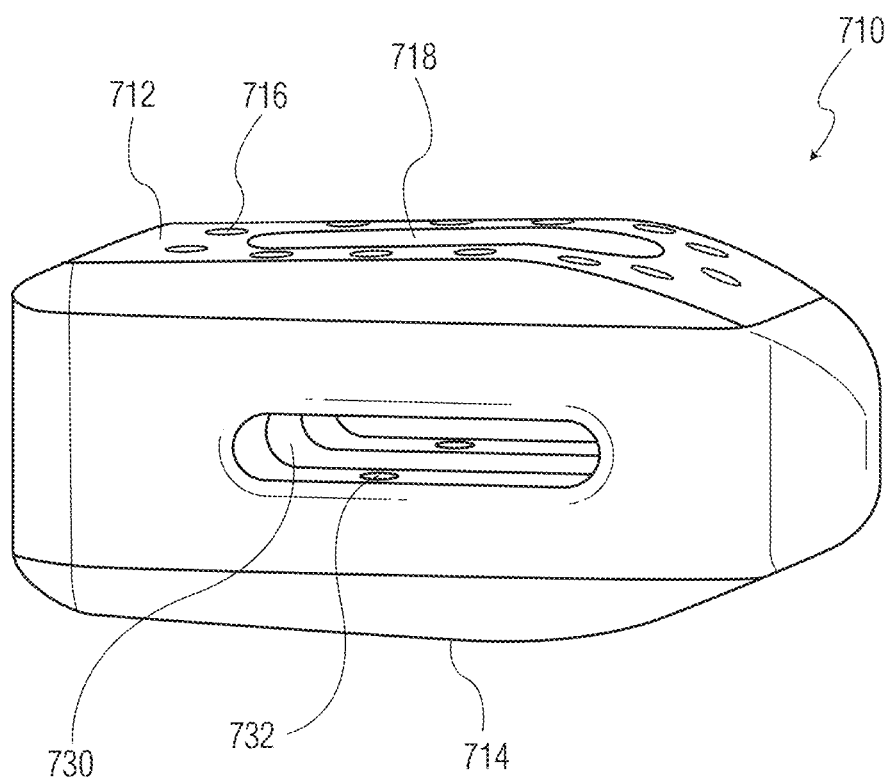
FIG. 8D depicts yet another implant embodiment of the present invention.

FIG. 8A depicts an implant 510 similar to above-discussed implant 10, while FIGS. 8B-8D depict implants 610 and 710 similar to above-discussed implant 410. As such, like reference numerals are utilized in such figures, where applicable. The implants of FIGS. 8A-D differ from the above-discussed implants in that they include lateral windows 530, 630 and 730, respectively, on each side of the implant. In each case, the lateral windows may allow for material introduced into the window to leach out and into the disc space. The windows may also act to reduce the overall stiffness of implants 510, 610 and 710 and to improve views during an imaging process (e.g., fluoroscopy). In this regard, it is contemplated that the windows may be tapered in a similar manner to the lordotic taper of the implant, where applicable. Furthermore, in the case of implant 710, lateral window 730 includes holes 732. These holes, like the others discussed above, allow for material introduced into the implant to pass therethrough.

Figure 9A:
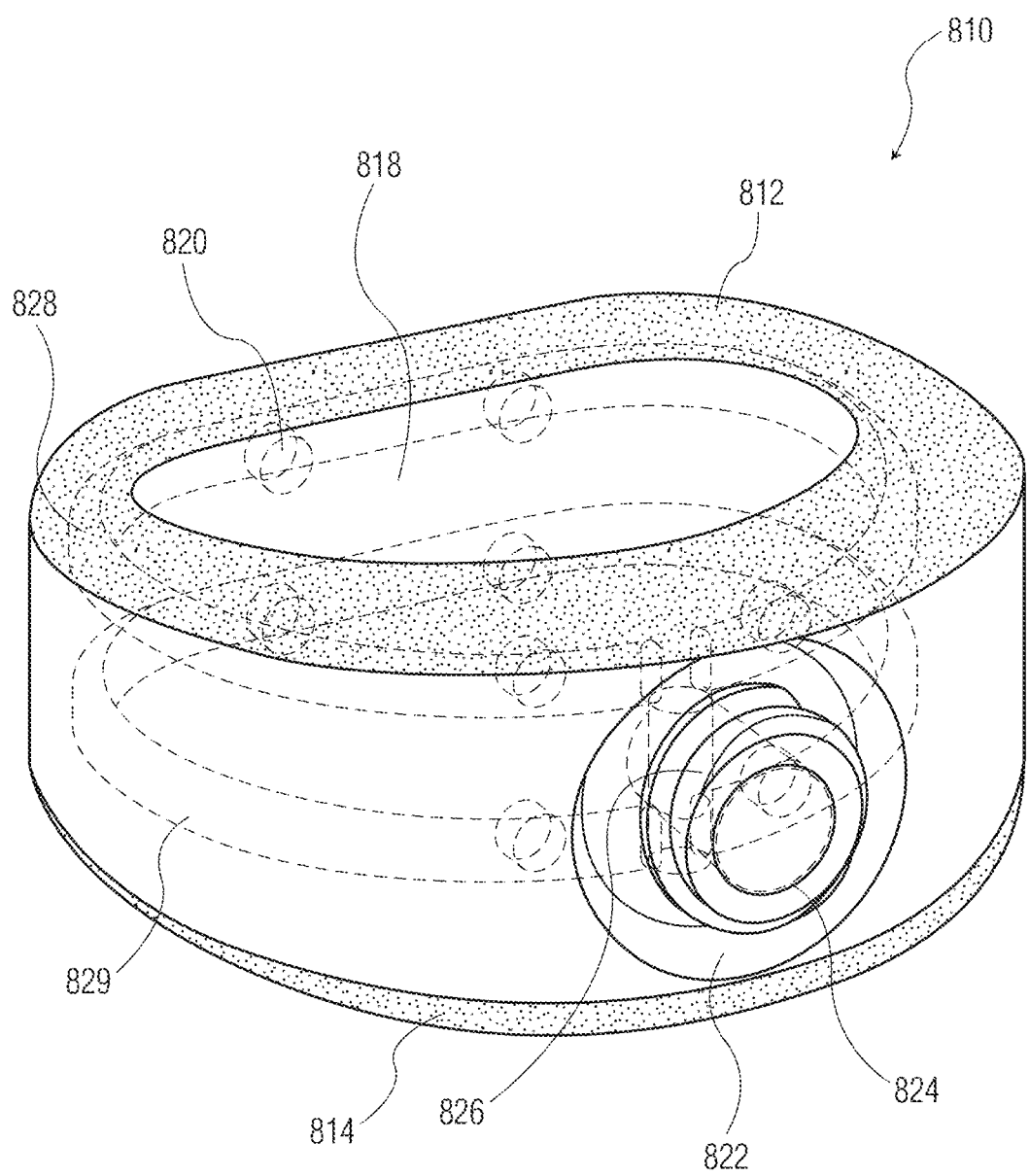
FIGS. 9A-9B depict yet another implant embodiment of the present invention.
Figure 9B:
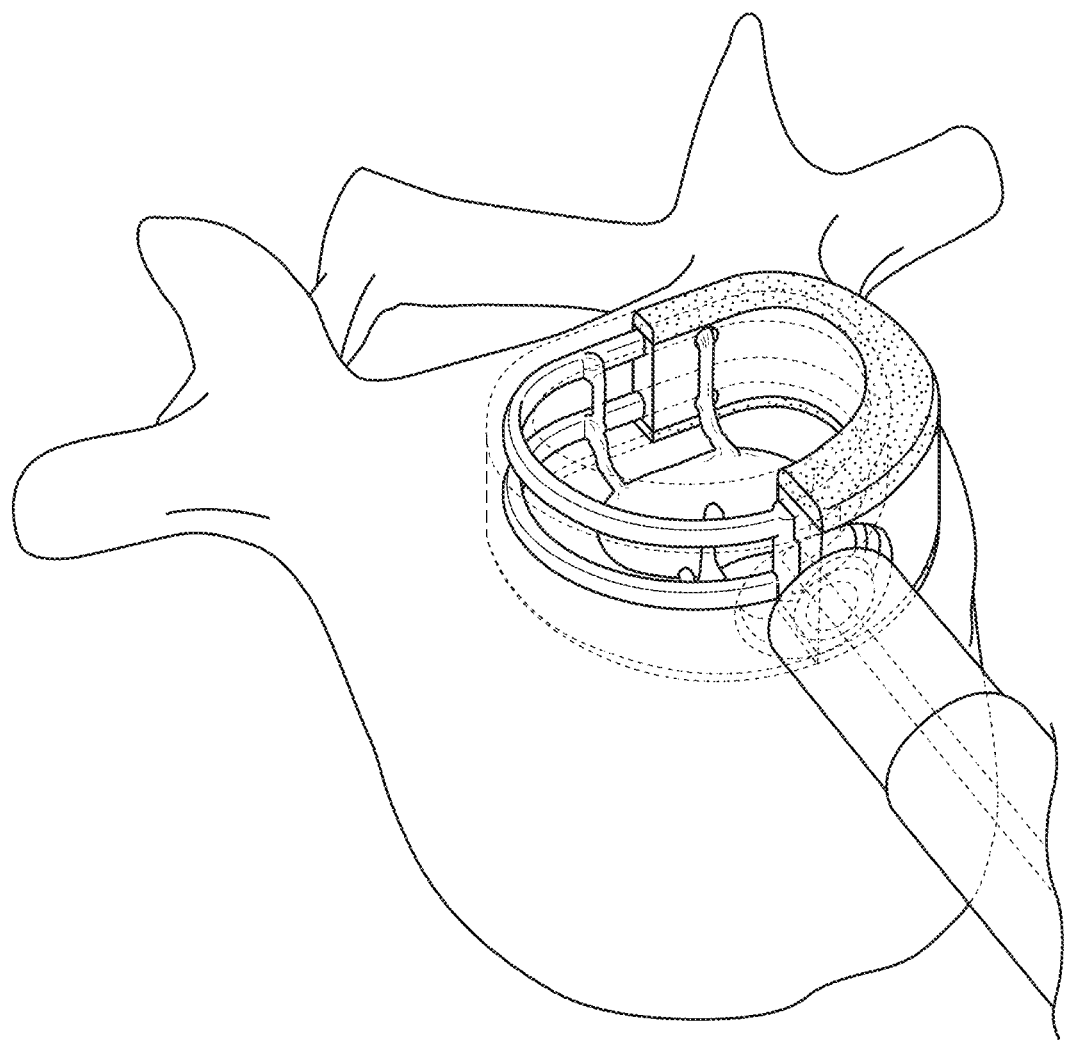

FIGS. 9A-9B depict yet another embodiment implant 810 similar to above-discussed implant 110. Most notably, implant 810 only includes holes 820 on an interior of cavity 818. Implant 810 also includes porous upper and lower surfaces 812, 814. The partial transparent view of FIG. 9A shows the inner components (e.g., manifold 826 and channels 828, 829), while the partial transparent implantation view of FIG. 9B shows the flow of material into cavity 818 and hence the disc space. It is noted that FIG. 9B does not include reference numerals so that the fluid flow can be fully appreciated.

Figure 10A:
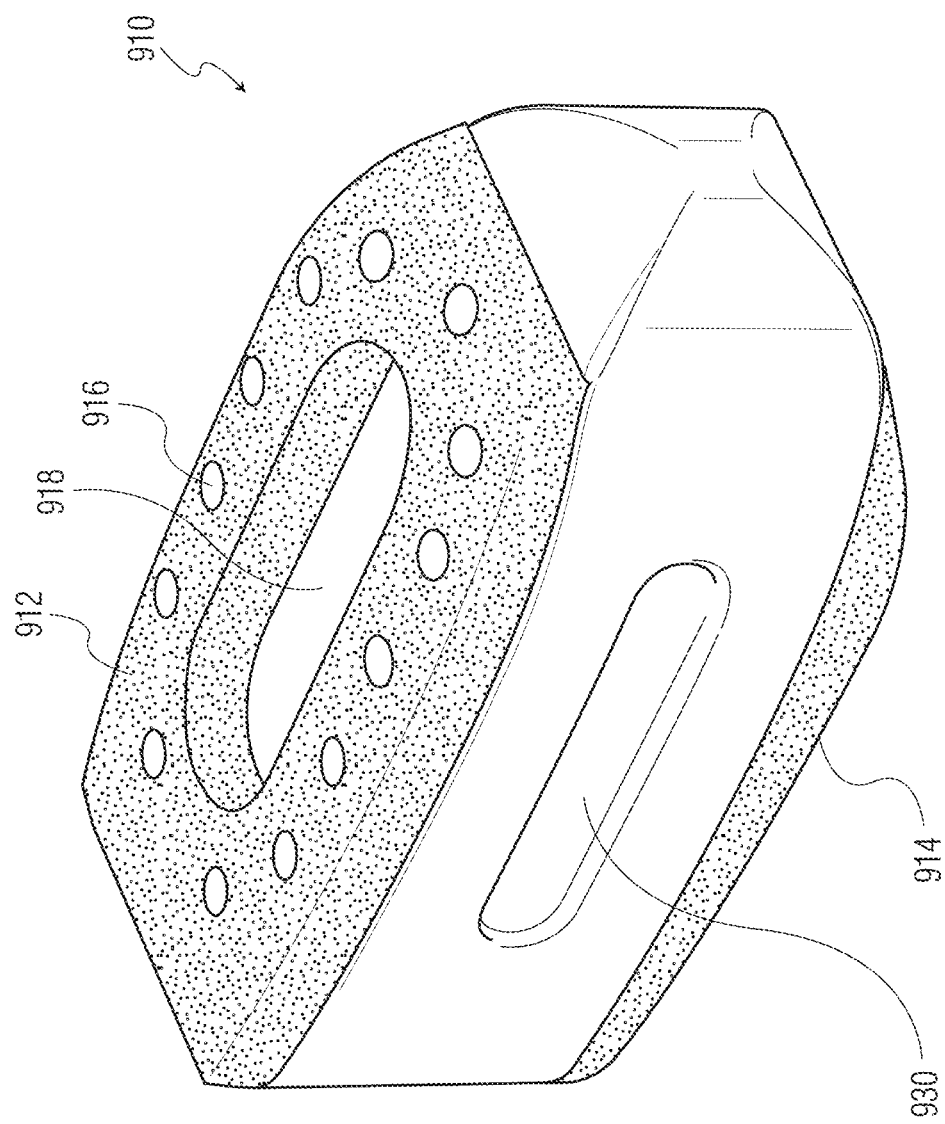
FIGS. 10A-10B depict yet another implant embodiment of the present invention.
Figure 10B:
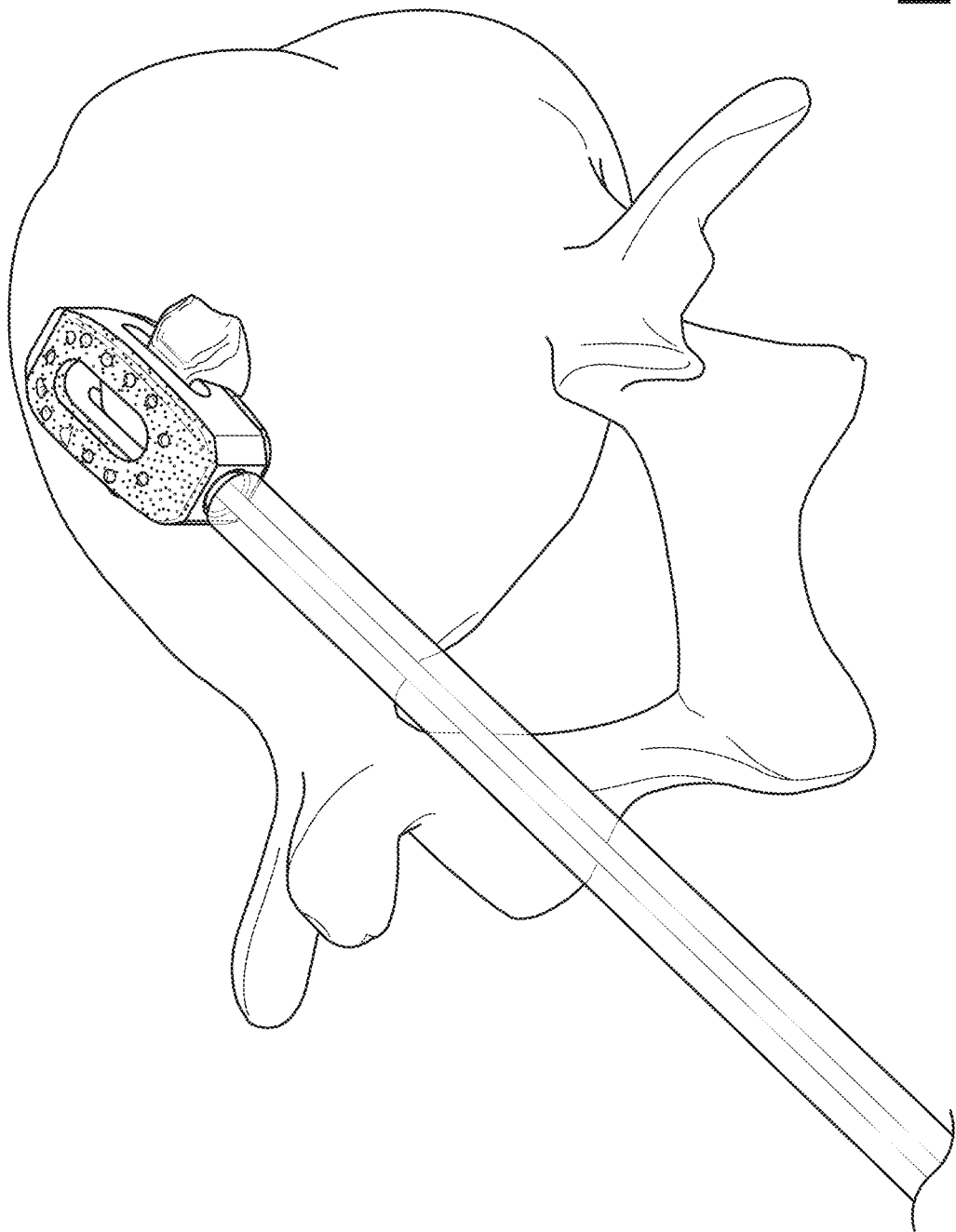

FIGS. 10A-10B depict an implant 910 similar to above-discussed implant 710. Implant 910 includes porous upper and lower surfaces 912, 914, as well as lateral windows 930 with holes 932. The partial transparent implantation view of FIG. 10B depicts the flow of material to upper surface 912, as well as from window 930. It is noted that FIG. 10B does not include reference numerals so that the fluid flow can be fully appreciated.

Figure 11A:
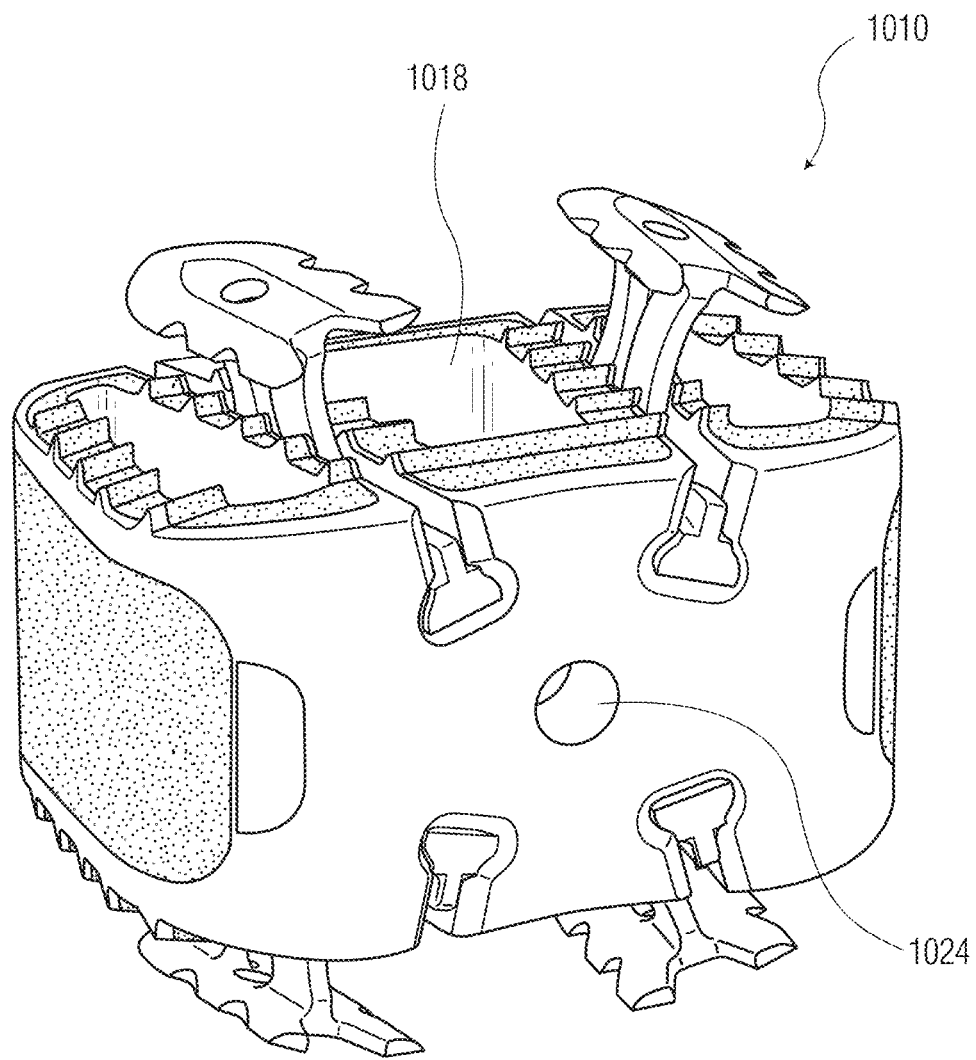
FIGS. 11A-11B depict yet another implant embodiment of the present invention.
Figure 11B:
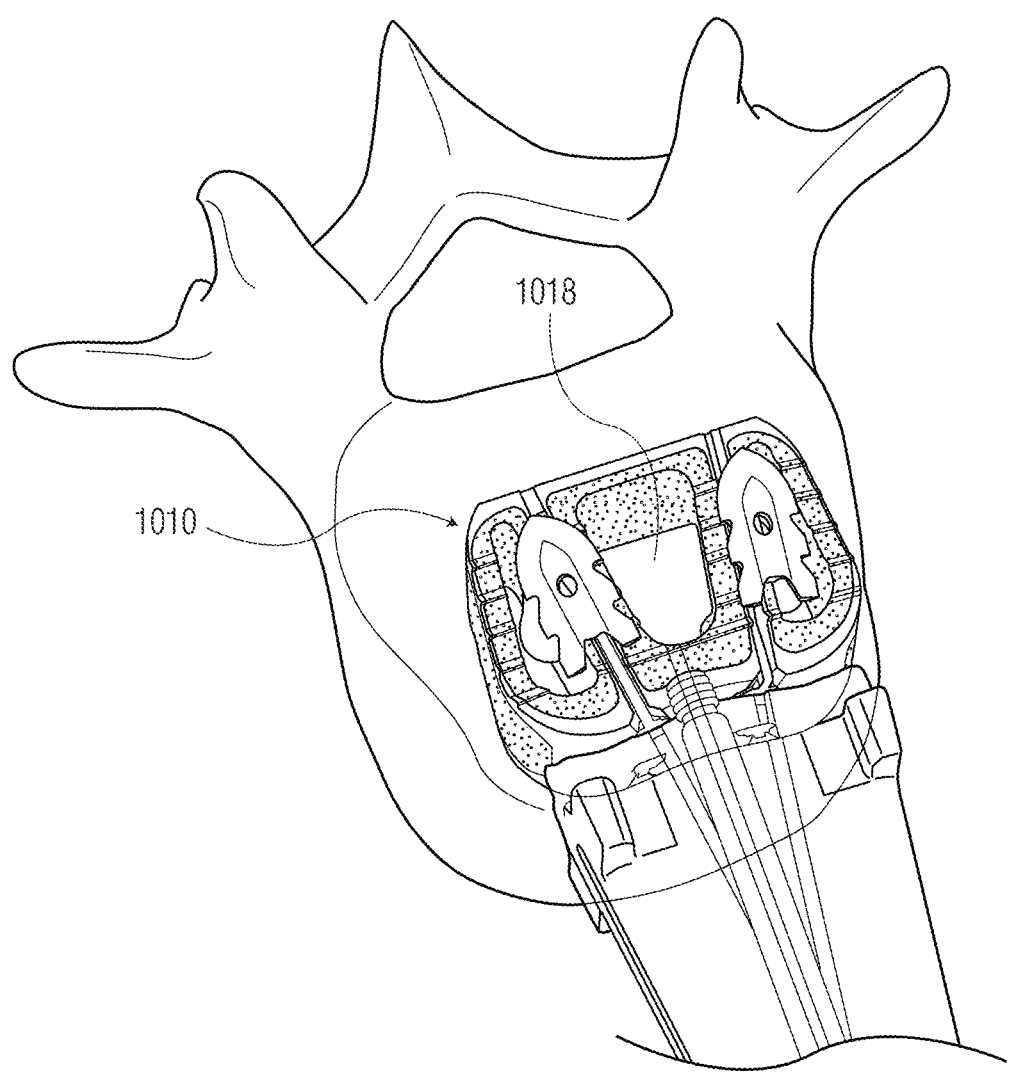

Implant 1010 of FIGS. 11A and 11B exhibits an overall design similar to that disclosed in U.S. Pat. No. 8,349,015 ("the '015 patent"), the disclosure of which is hereby incorporated by reference herein. In addition to employing a stand-alone design similar to that of the '015 patent, implant 1010, like those discussed above, includes a passage 1024 designed to fluidly engage an insertion tool. This allows for material to be introduced into implant 1010 where it is ultimately dispersed within cavity 1018. The flow of such material is shown in the partial transparent implantation view of FIG. 11B.

Figure 12A:
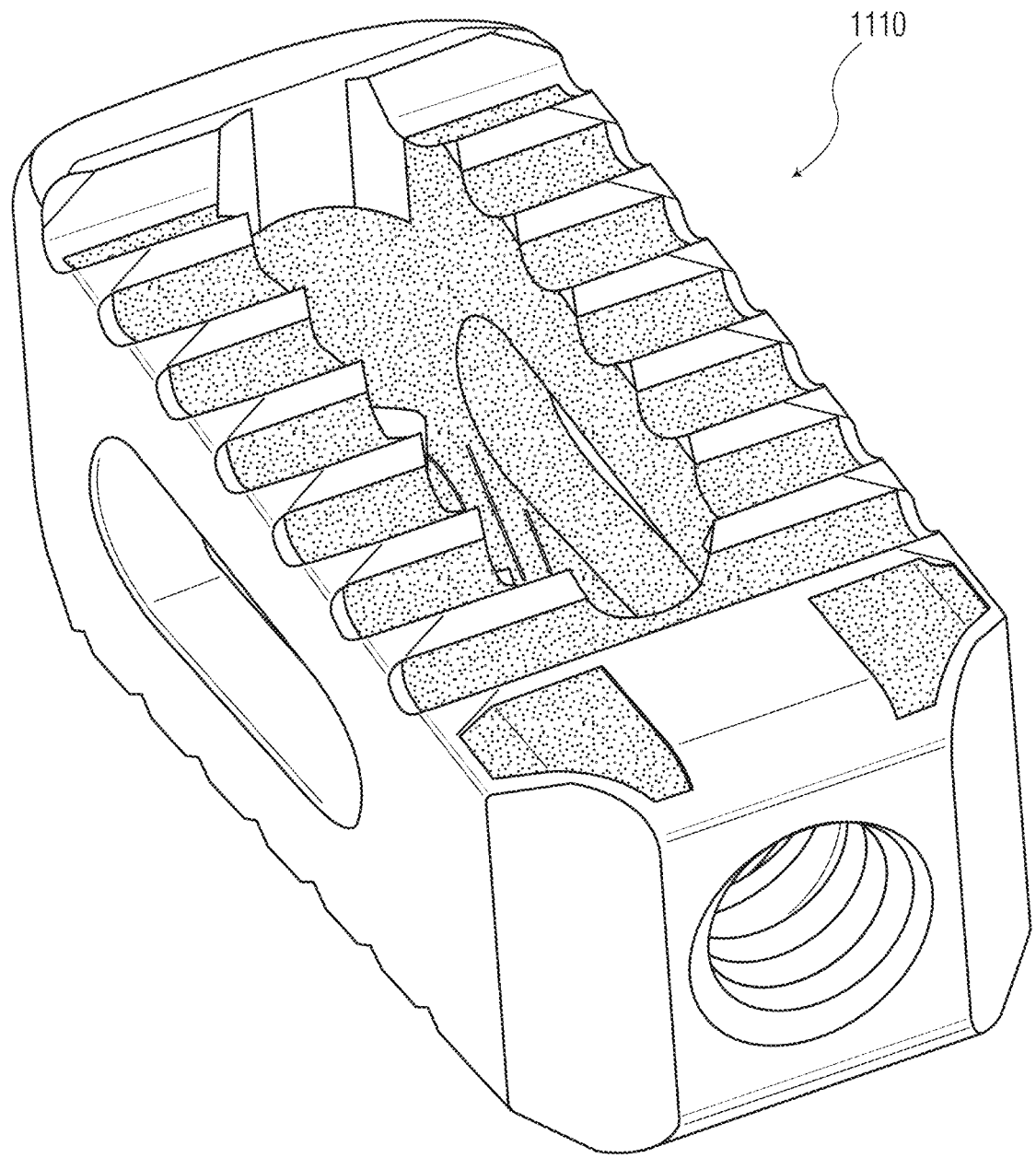
FIGS. 12A-12C depict yet another implant according to another embodiment of the present invention.
Figure 12B:
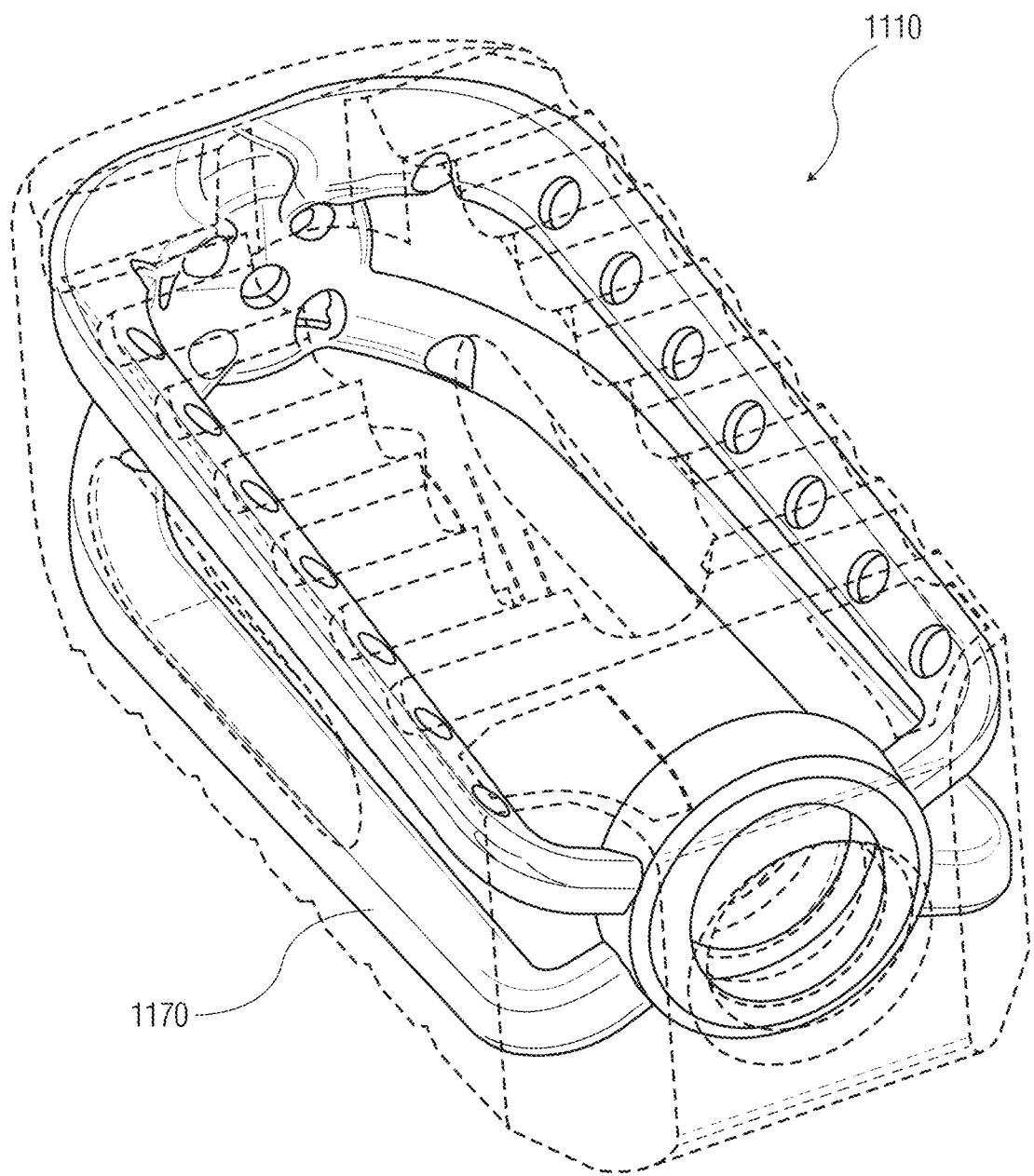
Figure 12C:
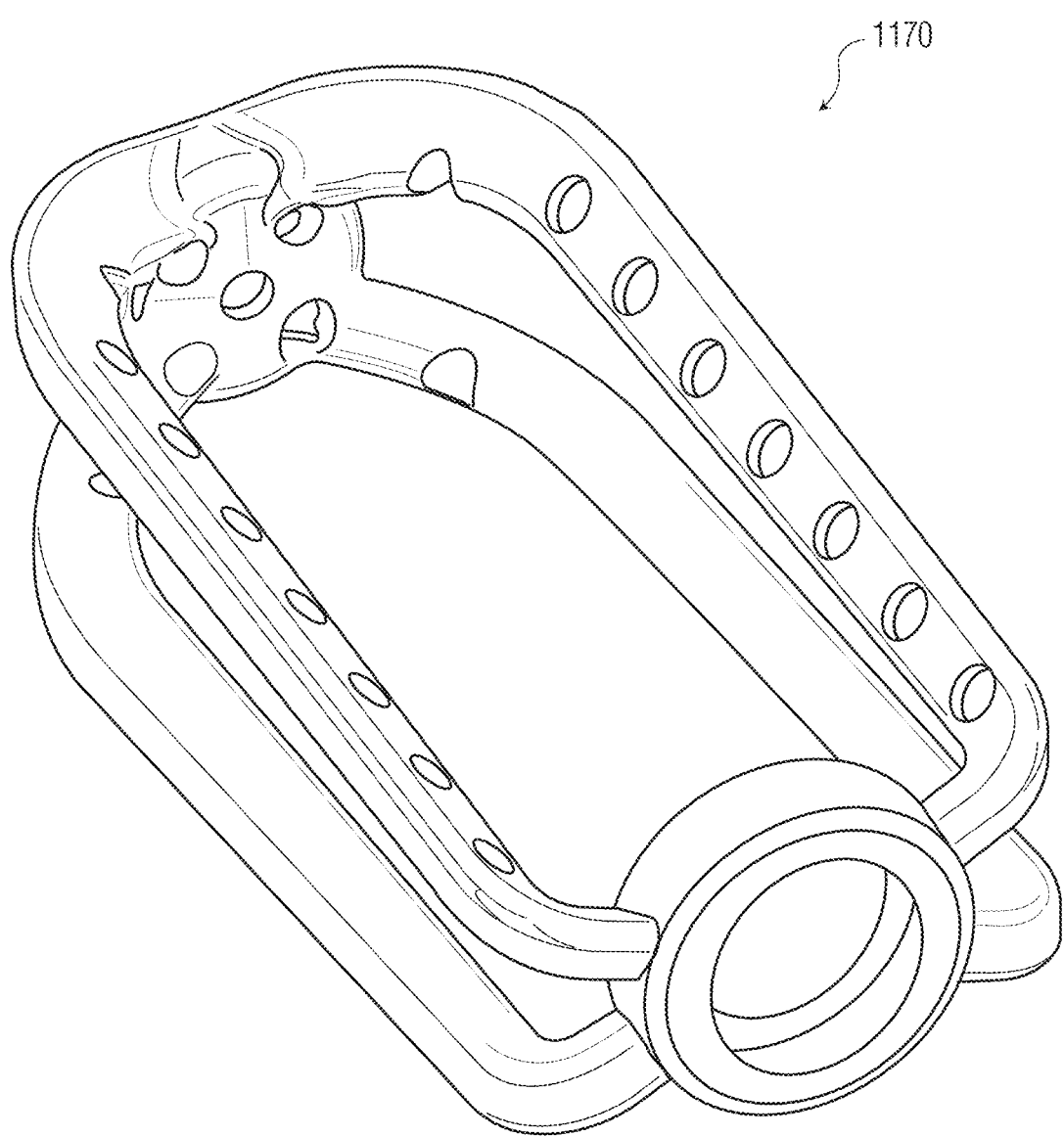

FIGS. 12A-12C depict an embodiment implant 1110, which is particularly suited for creation via a 3D printing or additive manufacturing process. In particular, in addition to including many similar elements to those discussed above in connection with the foregoing embodiments, implant 1110 includes a preformed fluid transfer structure 1170 (shown alone in FIG. 12C) that includes channels and holes formed therein. This component can be created separately from the remainder of implant 1110 and the can be built upon utilizing a 3D printing process or the like (see the partial hidden view of FIG. 12B). Additionally, the implant 1110 and the preformed fluid transfer structure 1170 can be created simultaneously. Alternatively, fluid transfer structure 1170 could be formed via a similar process. Implant 1110 exhibits a remaining structure similar to that disclosed in U.S. Provisional Patent Application No. 62/103,276, filed Jan. 14, 2015, and the related utility application filed on the same date as the present application, the disclosures of which is hereby incorporated herein by reference. For instance, the implant can exhibit exterior surfaces that include both porous and non-porous sections.

Figure 13:
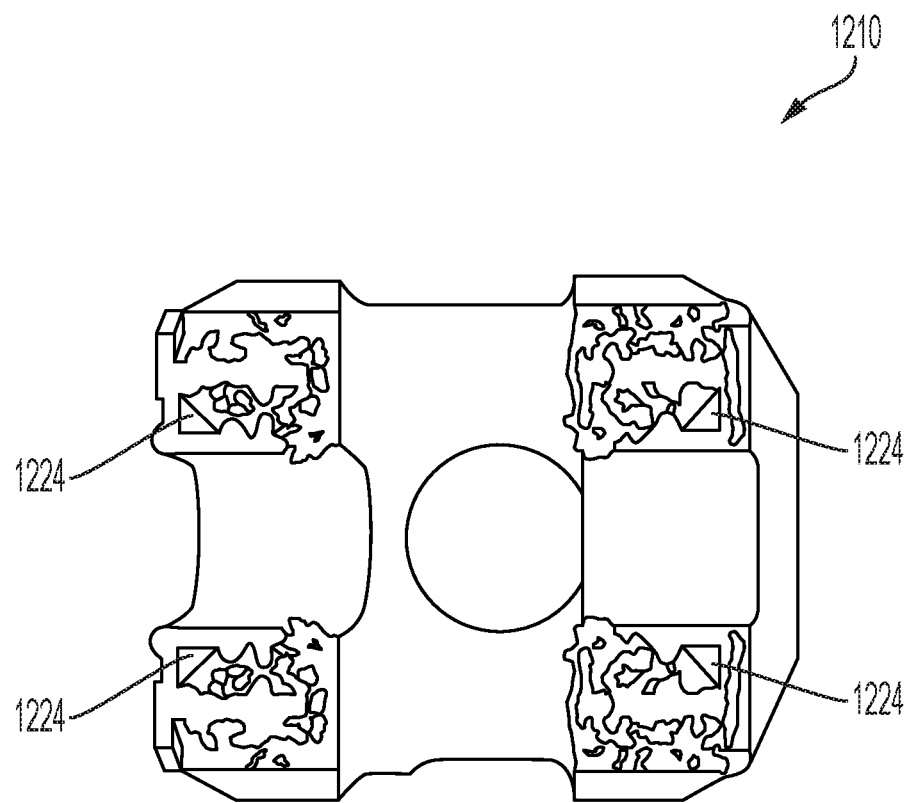
FIG. 13 is a cross-sectional view of an implant according to yet another embodiment of the present invention.

FIG. 13 depicts a cross-sectional view of yet another embodiment implant 1210. As shown, passages 1224 are simply formed as triangular shaped voids within the overall structure of the implant. It is noted that these passages may be in communication with holes (not shown) like those discussed above, or could simply allow for material to leach or push through the porous material making up implant 1210. In certain embodiments, this leaching may occur only at certain locations. Implant 1210 is yet another implant embodiment created utilizing a 3D printing process, but could of course be formed through the use of other known manufacturing processes.

The various embodiment implants disclosed in the present application make it readily apparent that implants according to the present invention may vary widely while still encompassing the salient features of the invention. It is to be understood that not all contemplated embodiments have been shown. It is also to be understood that the various embodiments may borrow certain features from each while still remaining within the scope of the present invention. It is also to be understood that although it is specifically discussed herein to create implants according to the present invention via a 3D printing like process, other processes may be utilized to manufacture the implants of the present invention.

Although shown as distinct passages, manifolds, channels and holes, it is contemplated to provide different formations for allowing for material to be introduced into implants according to the present invention and to be dispersed therefrom. For instance, it is contemplated to provide chambers that are in fluid communication with porous areas of the implant so that material within the chambers is allowed to pass through the porous material. The ability to include porous material in the implants themselves may negate the need for a specific passage/manifold/channel system. Moreover, it is contemplated to include independent passage/manifold/channel systems within a single implant. This, in connection with a multi-bore insertion tool may allow for the introduction of more than one material into the implant. For instance, it may be beneficial to have one material (e.g., allograft) directed to the cavity of the implant, while another material (e.g., cement) is directed to the upper and lower surfaces. It is also contemplated to provide holes on an exterior surface of the various implants, so as to allow material to be directed from the implant. This allows for such material to be dispersed around the implant, which may be beneficial in a fusion procedure. Of course, porous areas can also be included on the exterior of the implant to allow for same.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A spinal implant comprising:
an upper exterior surface including a first hole extending therefrom;
a lower exterior surface including a second hole extending therefrom;
a cavity formed through the upper and lower surfaces, the cavity being surrounded by a continuous inner wall extending between the upper and lower surfaces, the inner wall separating the cavity from a side exterior surface extending between the upper and lower surfaces, a third hole extending from the inner wall toward the side exterior surface; and
a fitting including a passage in fluid communication with the first, second and third holes via a first and second channel, the first and second channels being located between the inner wall and the side exterior surface and extending around the cavity such that the first and second channels form continuous pathways around the entire cavity.

2. The spinal implant of claim 1, further including a plurality of first, second and third holes.

3. The spinal implant of claim 2, further including a manifold in fluid communication with the passage, the first channel in fluid communication with the manifold and the first and third holes and the second channel in fluid communication with the manifold and the second and third holes.

4. The spinal implant of claim 3, wherein the first and second channels are curved.

5. The spinal implant of claim 4, wherein the manifold is curved.

6. The spinal implant of claim 3, wherein the first holes, second holes, first channel and second channel increase in size as they extend further away from the passage.

7. The spinal implant of claim 3, wherein the passage, the manifold, the first channel, the second channel and the first and second holes are included in a fluid transfer structure.

8. The spinal implant of claim 7, wherein the fluid transfer structure is formed separately from a remainder of the implant.

9. The spinal implant of claim 1, further including a porous structure at the upper and lower surfaces.

10. The spinal implant of claim 1, wherein the fitting is a male luer fitting.

11. The spinal implant of claim 1, further comprising a tool engaged with the fitting.

12. The spinal implant of claim 1, wherein the implant is designed to be implanted from an anterior aspect of a patient.

13. The spinal implant of claim 1, wherein the side exterior surface comprises sidewalls with windows, the windows in fluid communication with the cavity.

14. The spinal implant of claim 13, further comprising a fourth hole and a fifth hole located within the windows and in fluid communication with the passage.

15. A spinal implant comprising:
an upper exterior surface including a plurality of first holes extending therefrom;
a lower exterior surface including a plurality of second holes extending therefrom;
a cavity formed through the upper and lower surfaces, the cavity being surrounded by a continuous inner wall extending between the upper and lower surfaces, the inner wall separating the cavity from a side exterior surface extending between the upper and lower surfaces, a third hole extending from the inner wall toward the side exterior surface; and
a fitting including a passage in fluid communication with the first, second and third holes via a first and second channel, the first and second channels being located between the inner wall and the side exterior surface and extending around the cavity such that the first and second channels form continuous pathways around the entire cavity.

16. The spinal implant of claim 15, further including a manifold in fluid communication with the passage, the first channel in fluid communication with the manifold and the first and third holes, and the second channel in fluid communication with the manifold and the second and third holes.

* * * * *